United States Patent
Scholz et al.

(10) Patent No.: US 9,277,750 B2
(45) Date of Patent: *Mar. 8, 2016

(54) ANTISEPTIC COMPOSITIONS AND METHODS

(75) Inventors: Matthew T. Scholz, Woodbury, MN (US); Danli Wang, Shoreview, MN (US); Triet M. Lu, Woodbury, MN (US); Dong-Wei Zhu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 107 days.

This patent is subject to a terminal disclaimer.

(21) Appl. No.: 13/185,713

(22) Filed: Jul. 19, 2011

(65) Prior Publication Data

US 2011/0274770 A1 Nov. 10, 2011

Related U.S. Application Data

(60) Continuation of application No. 11/372,758, filed on Mar. 10, 2006, now Pat. No. 8,840,932, which is a division of application No. 10/051,719, filed on Jan. 16, 2002, now Pat. No. 7,147,873.

(51) Int. Cl.
*A01N 59/12* (2006.01)
*A01N 37/36* (2006.01)
*A01N 25/34* (2006.01)

(52) U.S. Cl.
CPC .............. *A01N 59/12* (2013.01); *Y10S 514/975* (2013.01)

(58) Field of Classification Search
CPC ....... A01N 59/12; A01N 25/24; A01N 37/36; Y10S 514/975
USPC ......................................................... 514/672
See application file for complete search history.

(56) References Cited

U.S. PATENT DOCUMENTS

| | | |
|---|---|---|
| 2,860,084 A | 11/1958 | Jackson |
| 3,216,983 A | 11/1965 | Shelanski et al. |
| 3,305,510 A | 2/1967 | Gander |
| 3,380,923 A | 4/1968 | Beach |
| 3,644,650 A | 2/1972 | Sabatelli et al. |
| 4,199,564 A | 4/1980 | Silver et al. |
| 4,356,229 A | 10/1982 | Brodnyan et al. |
| 4,358,567 A | 11/1982 | Hayama et al. |
| 4,387,217 A | 6/1983 | Schmolka |
| 4,542,012 A | 9/1985 | Dell |
| 4,584,192 A | 4/1986 | Dell et al. |
| 4,597,975 A | 7/1986 | Woodward et al. |
| 4,883,828 A | 11/1989 | Oakes et al. |
| 4,946,673 A | 8/1990 | Pollack et al. |
| 4,978,527 A | 12/1990 | Brink et al. |
| 5,013,763 A | 5/1991 | Tubesing et al. |
| 5,173,291 A | 12/1992 | Brink et al. |
| 5,227,161 A | 7/1993 | Kessler |
| 5,235,015 A | 8/1993 | Ali et al. |
| 5,408,022 A | 4/1995 | Imazato et al. |
| 5,419,902 A | 5/1995 | Kessler |
| 5,437,932 A | 8/1995 | Ali et al. |
| 5,462,714 A | 10/1995 | Talwalker et al. |
| 5,529,770 A | 6/1996 | McKinzie et al. |
| 5,543,074 A | 8/1996 | Hague et al. |
| 5,547,662 A | 8/1996 | Khan et al. |
| 5,554,361 A | 9/1996 | Dixon |
| 5,618,841 A | 4/1997 | Kross |
| 5,621,058 A | 4/1997 | Kondo et al. |
| 5,629,024 A | 5/1997 | Kessler et al. |
| 5,665,776 A | 9/1997 | Yu et al. |
| 5,681,802 A | 10/1997 | Fujiwara et al. |
| 5,720,984 A | 2/1998 | Ricketts |
| 5,763,412 A | 6/1998 | Khan et al. |
| 5,800,685 A | 9/1998 | Perrault |
| 5,807,957 A | 9/1998 | Samour et al. |
| 5,817,344 A | 10/1998 | Hoang et al. |
| 5,846,564 A | 12/1998 | Besse |
| 5,874,074 A | 2/1999 | Smith |
| 5,908,619 A * | 6/1999 | Scholz ........................ 424/78.02 |
| 5,908,693 A | 6/1999 | Delgado et al. |
| 5,914,300 A | 6/1999 | Fujiwara et al. |
| 5,951,993 A | 9/1999 | Scholz et al. |
| 5,958,436 A | 9/1999 | Hahn et al. |
| 6,034,129 A | 3/2000 | Mandeville, III et al. |
| 6,039,940 A | 3/2000 | Perrault et al. |
| 6,086,911 A | 7/2000 | Godbey |
| 6,123,933 A | 9/2000 | Hayama et al. |
| 6,194,530 B1 | 2/2001 | Klesse et al. |
| 6,228,354 B1 | 5/2001 | Jeng |
| 6,248,335 B1 | 6/2001 | Duan et al. |
| 6,251,967 B1 | 6/2001 | Perichaud et al. |
| 6,261,577 B1 | 7/2001 | Kessler |
| 6,277,881 B1 | 8/2001 | Santhanam et al. |
| 6,379,685 B1 | 4/2002 | Richter et al. |
| 6,432,426 B2 | 8/2002 | Kessler |
| 6,521,222 B1 | 2/2003 | Philippe et al. |
| 6,838,078 B2 | 1/2005 | Wang et al. |
| 6,951,642 B2 | 10/2005 | Scholz et al. |

(Continued)

FOREIGN PATENT DOCUMENTS

| | | |
|---|---|---|
| CA | 1 065 254 | 10/1979 |
| EP | 0 100 591 | 2/1984 |

(Continued)

OTHER PUBLICATIONS

Evonik Industries AG, Eudragit Technical Information, Dec. 2012, 7 pages.

(Continued)

*Primary Examiner* — Sue Liu
*Assistant Examiner* — Andriae M Holt

(57) ABSTRACT

A skin antisepsis composition comprising a comprising a (C1-4)alcohol and water in a ratio of at least 60:40, a hydroxycarboxylic acid, a cationic film-forming polymer, and at least one antimicrobial agent; and methods of using the composition are provided.

16 Claims, 2 Drawing Sheets

(56) References Cited

U.S. PATENT DOCUMENTS

| | | |
|---|---|---|
| 7,005,031 B2 | 2/2006 | Lucast et al. |
| 7,147,873 B2 | 12/2006 | Scholz et al. |
| 7,323,163 B2 | 1/2008 | Wang et al. |
| 2001/0036482 A1 | 11/2001 | Fredell et al. |
| 2003/0032352 A1 | 2/2003 | Chang et al. |
| 2003/0118629 A1 | 6/2003 | Scholz et al. |
| 2003/0149106 A1 | 8/2003 | Mosbey et al. |
| 2003/0175503 A1 | 9/2003 | Lucast et al. |
| 2003/0194447 A1 | 10/2003 | Scholz et al. |
| 2007/0298126 A1 | 12/2007 | Kessler et al. |

FOREIGN PATENT DOCUMENTS

| | | |
|---|---|---|
| EP | 0 514 760 | 11/1992 |
| EP | 0 754 444 | 1/1997 |
| GB | 200 806 | 6/1924 |
| GB | 962 955 | 7/1964 |
| GB | 962 956 | 7/1964 |
| GB | 1 186 117 | 4/1970 |
| GB | 1 186 177 | 4/1970 |
| GB | 1 293 407 | 10/1972 |
| GB | 2 108 386 | 5/1983 |
| GB | 2 344 997 A | 6/2000 |
| JP | A S49-102829 | 7/1971 |
| JP | B S46-023277 | 8/1971 |
| JP | 59-27816 | 2/1984 |
| JP | 5-286842 | 11/1993 |
| JP | 5-295317 | 11/1993 |
| JP | 7-69828 | 3/1995 |
| JP | 07-097317 | 4/1995 |
| JP | 7-165611 | 6/1995 |
| JP | 8-89779 | 4/1996 |
| JP | 8-325538 A2 | 12/1996 |
| JP | 9-500098 | 1/1997 |
| JP | 10-72323 | 3/1998 |
| JP | 11-228609 | 8/1999 |
| JP | 2983449 B2 | 9/1999 |
| JP | 11-269448 | 10/1999 |
| JP | 2000-229863 | 8/2000 |
| JP | 2001-527166 | 12/2001 |
| RU | SU 1565855 A1 | 3/1988 |
| WO | WO 86/05391 A1 | 9/1986 |
| WO | 94/23581 | 2/1994 |
| WO | 94/06297 | 3/1994 |
| WO | WO 96/20227 A1 | 7/1996 |
| WO | WO 96/23510 | 8/1996 |
| WO | 99/22934 | 5/1999 |
| WO | WO 01/28572 A1 | 4/2001 |

OTHER PUBLICATIONS

IGEPAL® CO-720; Product Data Sheet US000303, 2 pgs. (Oct. 2003).

*Poucher's Perfumes, Cosmetics and Soaps*, 10$^{th}$ Edition, Hilda Butler, ED., Kluwer Academic Publishers, London, 2000, Title page, Publication page, and pp. 435-436.

"Airvol Polyvinyl Alcohol" Product Bulletin, available as CELVOL polyvinyl alcohols, Celanese Ltd., Dallas, TX (undated).

ASTM E 1173-93, "Standard Test Method for Evaluation of a Pre-Operative Skin Preparation," *Annual Book of ASTM Standards*, vol. 11.05, Title page and pp. 381-383 (2001).

ASTM D 3278-96, "Standard Test Methods for Flash Point of Liquids by Small Scale Closed-Cup Apparatus," *Annual Book of ASTM Standards*, vol. 06.01, Title page and pp. 366-373 (2002).

Billmeyer, Jr., *Textbook of Polymer Science*, 2$^{nd}$ Edition, Wiley-Interscience, Title Page, Publication page, Table of Contents and pp. 84-89 (1971).

Block, *Disinfection, Sterilization, and Preservation*, 4$^{th}$ Edition, Lea & Febiger, Philadelphia, PA, Gottardi, "Chapter 8, Iodine and Iodine Compounds," Title page and pp. 152-166 (1991).

Butterfield, "The Selection of a Dilution Water for Bacteriological Examinations," *Journal of Bacteriology*, vol. 23, No. 355, Baltimore, MD, Title page and pp. 355-368 (1932).

Draize, "Dermal Toxicity," *Appraisal of the Safety of Chemicals in Foods, Drugs, and Cosmetics*, Association of Food and Drug Officials of the United States, Topeka, Kansas, Title page and pp. 46-59 (1959).

Providone-Iodine [online] United States Pharmacopeia monograph, USP-NF Online Aug. 1, 2002-Dec. 31, 2002 [retrieved on Aug. 20, 2002]. Retrieved from the Internet: <URL: www.uspnf.com>.

Written Opinion for PCT/US02/36927 (6 pgs.), Aug. 5, 2003.

International Preliminary Report on Patentability for PCT/US02/36927 (13 pgs), Jan. 20, 2004.

European Office Action dated Sep. 12, 2007 for EP 02 79 1259.1 (6 pgs.).

Hickey et al., "Control of the amount of free molecular iodine in iodine germicides," *J. Pharm Pharmacology*, Dec. 1997;49(12):1195-1199.

Hill and Casewell, "The in-vitro activity of povidone-iodinecream against *Staphylococcus aureus* and its bioavailability in nasal secretions," *J. of Hospital Infection*, Jul. 2000;45(3):198-205.

"Faulding Betadine Surgical Scrub" Chemwatch Material Safety Data Sheet, Oct. 11, 2001, Revision No. 2, Chemwatch 141535, 12 pgs.

* cited by examiner

ANTISEPTIC COMPOSITIONS AND METHODS

CROSS REFERENCE TO RELATED APPLICATIONS

This application is a continuation of U.S. patent application Ser. No. 11/372,758, filed Mar. 10, 2006, now pending, which is a division of U.S. patent application Ser. No. 10/051,719, filed Jan. 16, 2002, both of which are incorporated herein by reference.

BACKGROUND

The present invention relates to compositions that contain at least one antimicrobial agent intended primarily for tissue antisepsis, particularly skin antisepsis.

It is a standard practice in the industrialized world to disinfect the skin prior to any invasive procedure such as surgery, catheterization, or needle puncture to reduce the risk of infection. These products are often referred to as skin preps or simply "preps." It is particularly advantageous to customers to have a single product that can be used on both in-tact skin and mucosal tissue (e.g. vaginal, oral, nasal, and ocular tissue). Other sensitive tissues that antimicrobial products have been used on include acute and chronic wounds as well as burns. For all of these skin antiseptics it is desirable to achieve a very rapid microbial reduction so that the clinician can get on with the intended procedure.

Recently, there have been several alcohol-based antiseptics on the market for both presurgical and precatherization antisepsis. These products, while good rapid acting antiseptics due to the high alcohol content (e.g., typically at least about 60 wt-%), are only suitable for use on in-tact skin and are not suitable for use on sensitive tissues such as mucosal tissue, wounds, or burn tissue.

It is well known that none of the commercially available skin antiseptics kill all of the bacteria on the skin. For this reason, recent products have incorporated film-forming polymers that resist wash-off during surgery or exposure to fluids. Some of these products also require an organic remover solution or lotion to get the prep off the skin. This is inconvenient for the clinician and requires significant extra time.

Thus, there is still a need for antiseptics having increased speed and/or length of bactericidal activity on skin in a product that is delivered out of an aqueous solution, that preferably dries to a coating with little or no tack, and that preferably allows adhesion of PSA-coated products.

SUMMARY

The present invention relates to compositions that contain at least one antimicrobial agent. Such compositions are intended primarily for tissue antisepsis, and more particularly, skin antisepsis. Surprisingly, the compositions of the present invention are gentle and thus useful on mucosal tissue as well as in-tact skin.

Compositions of the present invention include iodine ($I_2$), an iodophor, or a combination thereof, a hydroxycarboxylic acid buffer in an amount of at least about 5 wt-%, water, and optionally a film-forming polymer, preferably having both hydrophilic and hydrophobic moieties. Surprisingly, despite the high level (at least about 5 wt-%) of hydroxycarboxylic acid buffers, which are very hydrophilic, preferred compositions of the present invention remain generally nontacky when dry and allow for prolonged adhesion of pressure sensitive adhesive (PSA) coated products. Furthermore, for compositions that include polymeric film formers along with the relatively high level of hydroxycarboxylic acid buffers, it is surprising that they do not precipitate out of the compositions immediately or over time (i.e. salt out of solution).

Significantly, preferred compositions of the present invention reduce normal skin flora by at least about 1 log (i.e., 10-fold) reduction, often at least about 1.5 log reduction, and more often at least about 2 log (i.e., 100-fold) reduction, on a dry human skin site (typically, a back or abdomen) in only 2 minutes when tested according to ASTM testing method E1173-93 and a 30-second scrub with gauze soaked in the composition using moderate pressure.

In one embodiment, the present invention provides an antiseptic composition that includes: an antimicrobial agent selected from the group consisting of iodine ($I_2$), an iodophor (i.e., a complex of iodine or triiodide with a carrier that is capable of generating elemental iodine under use conditions, such as povidone-iodine), and combinations thereof, wherein the antimicrobial agent is present in an amount sufficient to provide an available iodine concentration of at least about 0.25 wt-% (preferably, an available iodine concentration of no greater than about 1.0 wt-%); a hydroxycarboxylic acid buffer in an amount of at least about 5 wt-% (preferably, in an amount of no greater than about 15% by weight); water; and a film-forming polymer (preferably in an amount of at least about 2 wt-%), which is preferably substantive, thereby resulting in a substantive composition. Preferably, the weight ratio of the film-forming polymer to hydroxycarboxylic acid buffer is at least about 0.25:1.

Preferably, the compositions of the present invention include one or more surfactants, which can be nonionic, anionic, or amphoteric. Preferred nonionic surfactants have an HLB value of at least about 14. In certain embodiments, preferred surfactants are anionic or amphoteric surfactants selected from the group consisting of sulfonates, sulfates, phosphates, phosphonates, and ammonium sulfonate amphoterics, and mixtures thereof. In certain other embodiments, a preferred surfactant is an amine oxide. Various mixtures of such surfactants can be used if desired.

In another embodiment, the present invention provides an antiseptic composition that includes: an antimicrobial agent selected from the group consisting of iodine ($I_2$), an iodophor, and a combination thereof, wherein the antimicrobial agent is present in an amount sufficient to provide an available iodine concentration of at least about 0.25 wt-%; a hydroxycarboxylic acid buffer in an amount of at least about 5 wt-%; water; and a substantive film-forming polymer; wherein a dry film of the composition is stable and substantive.

In still another embodiment, the present invention provides an antiseptic composition that includes: an antimicrobial agent selected from the group consisting of iodine ($I_2$), an iodophor, and a combination thereof, wherein the antimicrobial agent is present in an amount sufficient to provide an available iodine concentration of at least about 0.25 wt-%; a hydroxycarboxylic acid buffer in an amount of at least about 5 wt-%; water; and a film-forming polymer that includes hydrophilic and hydrophobic moieties.

In still another embodiment, the present invention provides an antiseptic composition that includes: an iodophor in an amount of greater than 5 wt-%, wherein the iodophor comprises a carrier selected from the group consisting of a polyvinylpyrrolidone, a copolymer of N-vinyl lactam, a polyether glycol, a polyvinyl alcohol, a polyacrylamide, a polysaccharide, and combinations thereof; a hydroxycarboxylic acid buffer in an amount of at least about 5 wt-%; and water.

In another embodiment, the present invention provides an antiseptic composition that includes: an antimicrobial agent selected from the group consisting of iodine (I$_2$), an iodophor, and a combination thereof, wherein the antimicrobial agent is present in an amount sufficient to provide an available iodine concentration of at least about 0.25 wt-%; a hydroxycarboxylic acid buffer in an amount of at least about 5 wt-%; water; and a substantive film-forming polymer. The dry film of the composition is stable and substantive and demonstrates one or more of the following characteristics: reduces normal skin flora by at least about 1 log in 2 minutes on a dry human skin site using ASTM testing method E1173-93 and a 30-second scrub with gauze soaked in the composition using moderate pressure; is substantially nontacky when in the form of a dry film; demonstrates a Draize score of zero in no greater than about 96 hours according to the Rabbit Eye Irritation Test; or adheres to a PSA-coated tape at a level of at least about 50% of the level of adhesion of the PSA-coated tape applied over dried BETADINE surgical scrub and paint solutions when measured using a 180 degree peel test after applying the PSA-coated tape to a dry film on dry human skin by rolling with a 2.1-kg, 5.1-cm wide roller, waiting at least 1 minute, and removing the PSA-coated tape at a peel angle of 180 degrees at a speed of 30.5 cm/minute.

In yet another embodiment, the present invention provides an antiseptic composition that includes: an antimicrobial agent selected from the group consisting of iodine (I$_2$), an iodophor, and a combination thereof, wherein the antimicrobial agent is present in an amount sufficient to provide an available iodine concentration of at least about 0.25 wt-% to about 1.0 wt-%; a hydroxycarboxylic acid buffer in an amount of about 5 wt-% to about 15 wt-%; water; and a substantive film-forming polymer; wherein the hydroxycarboxylic acid buffer includes a compound represented by the formula:

$$R^1(CR^2OH)_n(CH_2)_mCOOH$$

wherein: R$^1$ and R$^2$ are each independently H or a (C1-C8) saturated straight, branched, or cyclic alkyl group, a (C6-C12)aryl group, or a (C6-C12)aralkyl or alkaryl group wherein the alkyl groups are saturated straight, branched, or cyclic, wherein R$^1$ and R$^2$ may be optionally substituted with one or more carboxylic acid groups; m=0 or 1; and n=1-3.

The present invention also provides methods of disinfecting tissue, e.g., skin or mucosal tissue. In one embodiment, the present invention provides a method of disinfecting tissue including: applying directly to tissue (by this it is meant that the composition is not diluted) an antiseptic composition that includes: an antimicrobial agent selected from the group consisting of iodine (I$_2$), an iodophor, and a combination thereof, wherein the antimicrobial agent is present in an amount sufficient to provide an available iodine concentration of at least about 0.25 wt-%; a hydroxycarboxylic acid buffer in an amount of at least about 5 wt-%; and water; and allowing the antiseptic composition to remain on the tissue. Preferably, the antiseptic composition further includes a film-forming polymer, which is preferably substantive.

Various other methods are provided that use the compositions of the present invention to disinfect. These methods involve applying the composition to tissue directly (i.e., undiluted) and allowing it to remain on the tissue. Such methods are in contrast to the conventional way in which soaps and shampoos are used, which involves immediate dilution during use and thorough rinsing immediately after application. That is, the antiseptic compositions of the present invention are intended to remain on the tissue for a time sufficient to reduce the bacterial load on the tissue. This is possible due to the very low irritation potential of the compositions of the present invention.

The present invention also provides methods of making antiseptic compositions. One such method involves combining components that include: an antimicrobial agent selected from the group consisting of iodine (I$_2$), an iodophor, and a combination thereof, wherein the antimicrobial agent is present in an amount sufficient to provide an available iodine concentration of at least about 0.25 wt-%; a hydroxycarboxylic acid buffer in an amount of at least about 5 wt-%; water; and a substantive film-forming polymer. Preferably, the hydroxycarboxylic acid buffer and antimicrobial agent are combined and then the substantive film-forming polymer is added.

Herein, the following definitions are used:

"dry human skin site" refers to the back or abdomen of a person;

"film-forming" refers to a composition when allowed to dry under ambient conditions (e.g., 23° C. and 50% relative humidity (RH)) on in-tact skin forms a continuous layer that does not flake off after simple flexing of the tissue;

"hydroxycarboxylic acid buffer" refers to free acids, as well as lactones thereof, salts thereof, and/or derivatives thereof as described in greater detail below;

"normal skin flora" refers to resident skin flora present on the skin of a healthy person and often consists of predominantly of *Staphylococcus epidermidis*;

"polymer" includes homopolymers and copolymers and "copolymer" includes a polymer of any length (including oligomers) of two or more types of polymerizable monomers, and therefore includes terpolymers, tetrapolymers, etc., which can include random copolymers, block copolymers, or sequential copolymers;

"side-chain" refers to the portion of a monomer which following polymerization forms a branch off the polymer backbone (i.e., main chain); in a vinyl polymer, it is a group of two or more atoms that branch off from the straight chain of carbon atoms formed by vinyl polymerization;

"stable" refers to an antiseptic composition that shows no signs of visible gross phase separation (precipitation, phase split, settling, etc.) after storage at 50° C. for 5 days (preferably 10 days, more preferably 20 days, and most preferably 30 days); certain samples may become slightly cloudy during storage at 50° C. for 5 days, however, since there is no gross precipitation and/or settling these samples are considered to be physically stable, but the most stable samples show no visible changes, i.e., no changes in clarity, color, etc.;

"substantially nontacky" refers to a dry film of about 4 milligrams composition per square centimeter (mg/cm$^2$) of human skin on a forearm that demonstrates little or no tack to a clean dry thumb (washed with a lotion-free soap such as IVORY bar soap (Proctor and Gamble, Cincinnati, Ohio) and dried thoroughly immediately prior to use) when pressed onto the dry film and immediately removed;

"substantive" as it applies to an antiseptic composition (or a film-forming polymer) means that when an antiseptic composition (or a film-forming polymer in solution) is applied to human skin as a uniform wet film in an amount of approximately 4 milligram per square centimeter (mg/cm$^2$) clean dry skin on an inner forearm and allowed to thoroughly dry (e.g., at least 10 minutes at 23° C. and 50% relative humidity), it resists removal under running tap water at a temperature of about 23° C. to about 24° C. and a flow rate of about 2.4-2.5 liters/minute (L/min) falling from a height of 15 centimeters (cm) and striking the skin immediately above the dry composition (not directly on the dry composition) and then flowing over the dry composition for at least about 15 seconds;

"use concentration" refers to the concentration of a composition actually applied to the skin; and "wound" refers to an injury to mammalian tissue that involves breaking of a membrane such as the skin or mucosal surface usually with damage to underlying tissue arising from, but not limited to, a surgical incision, puncture, laceration, or burn.

DETAILED DESCRIPTION OF PREFERRED EMBODIMENTS

Figure 1:
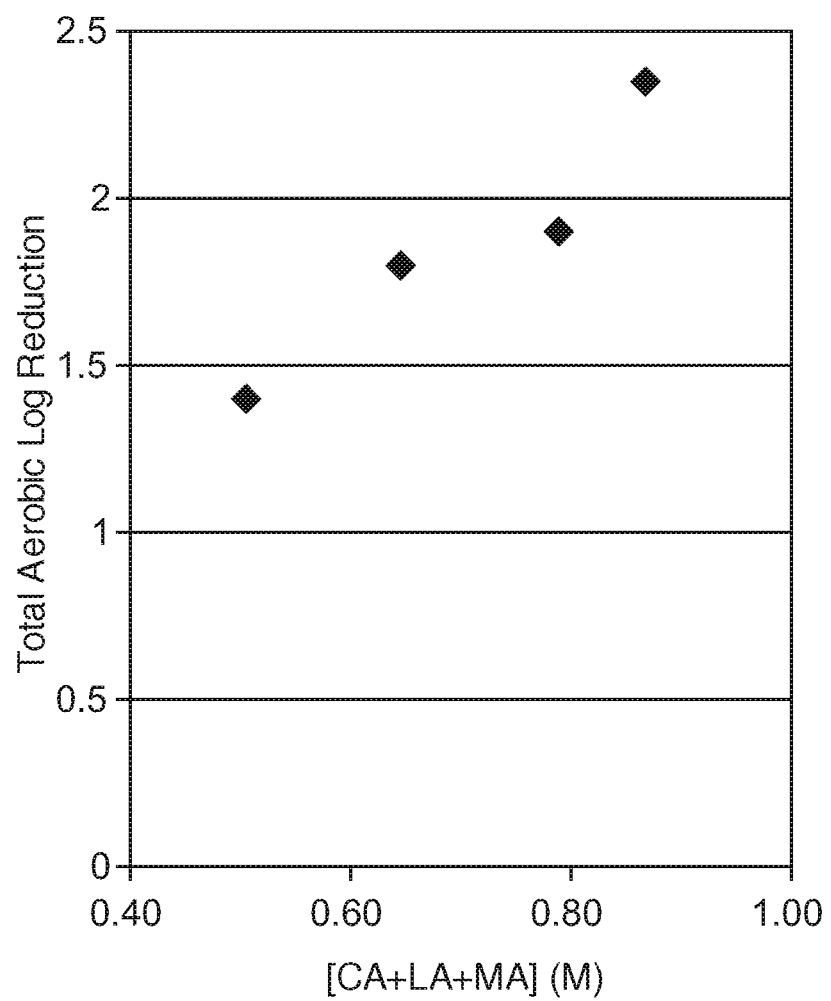
FIG. 1. Antimicrobial activity results plotted as a function of total molar concentration of alpha-hydroxy acid.

Desirable antiseptic compositions are aqueous-based and have the following characteristics: relatively high levels of bacterial kill; relatively short dry times; generally clear viewing of the underlying tissue; good adhesion to the skin when dry; little or no tack when dry; capable of releasing an antimicrobial agent over a period of time; good adhesion of pressure sensitive adhesive (PSA) coated products such as incise drapes, tapes, wound dressings, and the like; resist lift off of PSA-coated products while under stress as typically occurs during retraction in surgery; allow adhesion of PSA-coated products for long periods of time, e.g., hours to days; suitable for use on sensitive tissues such as mucosal tissue; and can be removed relatively easily, preferably without the need for organic solvent-based removers.

Preferred antiseptic compositions of the present invention possess all of the above-mentioned characteristics. Significantly, they provide rapid microbial kill, and they dry to low tack or nontacky films, which allow good adhesion of PSA-coated products. Furthermore, they are gentle to tissue and can be removed with a water-soaked fabric, such as a towel or simple gauze.

Furthermore, preferred compositions of the present invention are very stable and can survive prolonged exposure to elevated temperatures, e.g., 50° C. and even as high as 60° C., for prolonged periods of time, e.g., for often greater than 7 days. The most stable samples show no visible changes at all such as changes in color, turbidity, and the like. Also, preferred compositions of the present invention are very stable upon exposure to low temperatures, e.g., 4° C., and even during repeated freeze/thaw cycles, e.g., 2 or more cycles.

Preferred compositions of the present invention are also generally substantive. More preferred compositions of the present invention are substantive while in moist environments, such as the vaginal vault and remain in the vagina for longer periods of time than typical antiseptics such as BETADINE 10% povidone-iodine solution (Purdue Frederick, Norwalk, Conn.). A "substantive" composition is one that when tested as described above resists removal for at least about 15 seconds. Preferably, the compositions are even more substantive and resist being removed under the same conditions for at least about 30 seconds, more preferably at least 45 seconds, and most preferably at least about 60 seconds. This is conveniently determined by imparting color to the composition (e.g., inclusion of a small amount of a dye or a colored active such as povidone-iodine in sufficient concentration that a relatively dark color results on the skin that can be easily seen as present or not).

The dried films of preferred antiseptic compositions of the present invention that include a film-forming polymer are generally flexible and durable. That is, they do not crack or flake off as brittle films might do. Significantly, the film-forming polymer contributes to achieving a delicate balance between low tack and flexibility.

Preferred compositions of the present invention also possess viscosities that ensure the formulations go on easily and form a relatively thin film that can dry rapidly. Preferably, the Brookfield viscosity (as described in the Examples Section) of a composition is no greater than about 1000 Centipoise (cps), more preferably no greater than about 500 cps, even more preferably no greater than about 250 cps, even more preferably no greater than about 100 cps, and most preferably no greater than about 50 cps, when measured at 23° C. using a Brookfield RVT ROTOVISCO viscometer and the procedure described in the Examples Section. This low viscosity ensures that the composition can be painted on the skin with little effort in a uniform thin film that will dry rapidly.

Dry times are preferably no greater than about 5 minutes, more preferably no greater than about 3 minutes, even more preferably no greater than about 2 minutes, and most preferably no greater than about 1.5 minutes on human skin measured at 23° C. at 45-55% relative humidity. Dry time is measured as the minimum time for a composition applied with gauze in a uniform thin film of about 3 mg composition/$cm^2$ of skin to be visibly dry, demonstrate no transfer of the composition to a latex gloved covered hand, and have a minimum level of tack. An average of at least five subjects is typically used.

A particularly important property of the compositions of the present invention is the ability to reduce the bacterial load on tissue, particularly skin, i.e., to kill the natural skin flora, rapidly. Preferably, compositions of the present invention are capable of reducing normal skin flora by at least about 1 log (10-fold), more preferably by at least about 1.5 log, and most preferably by at least about 2 logs (100-fold), in 2 minutes on a dry human skin site (typically, skin on an abdomen or back) using ASTM testing method E1173-93 and a 30-second scrub with gauze soaked in the composition using moderate pressure.

This surprising rapid and high antimicrobial activity is provided through the use of iodine or an iodophor as the active antimicrobial agent in combination with one or more hydroxycarboxylic acid buffers in particularly high use concentrations. The hydroxycarboxylic acid buffer in the compositions of the present invention contributes significantly to such good bacterial kill. By comparison, a composition of the present invention reduces normal skin flora by at least about 0.5 log more than the same composition without the hydroxycarboxylic acid buffer present. This "same" composition includes additional water instead of the hydroxycarboxylic acid buffer and would be adjusted to the same pH as the composition with the hydroxycarboxylic acid buffer.

Surprisingly, the placebo compositions (i.e., compositions without an antimicrobial agent) but still including the hydroxycarboxylic acid buffer are relatively inactive. By comparison, a composition of the present invention reduces normal skin flora by at least about 0.5 log more than the same composition without the antimicrobial agent present when tested on a dry human skin site (e.g., back or abdomen) according to ASTM testing method E1173-93 measured 2 minutes after completion of a 30-second scrub with gauze soaked in the composition using moderate pressure.

Generally, antiseptic compositions are applied to the tissue, typically skin, and allowed to dry and remain in place for at least 2 minutes, and often for several hours to days. Significantly, many of the compositions of the present invention maintain very low bacterial counts on the tissue, typically skin, for long periods of time, e.g., often up to 6 hours, and even up to 24 hours.

Antimicrobial Agent

A preferred active antimicrobial agent is elemental iodine ($I_2$). As in most iodine-containing patient preps, other iodine-containing species may be present in addition to iodine. Such species include, for example, hypoiodous acid (HOI), iodide ($I^-$), triiodide ($I_3^-$), iodate ($IO_3^-$) and the like. It is widely recognized that elemental iodine is the most active antimicrobial species. See, for example, Disinfection, Sterilization, and Preservation by Seymour S. Block, $4^{th}$ edition, Chapter 8 "Iodine and Iodine Compounds," Lea & Febiger, Philadelphia Pa., 1991.

In most commercially available iodine disinfectants, in order to prevent rapid reduction of iodine to iodide the solutions are typically buffered to be slightly acidic. The acidity is typically required to maintain stability in the iodine solutions and to suppress conversion to other iodine species that are less germicidal. For example, commercial skin preps containing iodine generally have pH values in the range of 3 to 5, which favors stability of the molecular iodine species. HOI normally exists in very low levels relative to $I_2$ but has been reported as an effective antimicrobial and may contribute to kill in some compositions. $IO_3^-$ is an effective oxidant only at pH values less than 4, where significant amounts of $HIO_3$ can exist.

As further background for understanding and practicing the present invention, elemental iodine is only slightly soluble in water (0.03 wt-% at 25° C.). Alkali metal iodides, which combine with iodine to form triiodide ($I_3$), increase that solubility. Molecular iodine, however, can be very irritating at higher concentrations. For example, Lugol's solution (5% elemental iodine and 10% potassium iodide) and tincture of iodine (45% aqueous ethanol with 2% elemental iodine and 2.4% sodium iodide) have both been well documented to be quite irritating to the skin.

Many references have described the preparation of "iodophors," which are complexes of elemental iodine or triiodide with certain carriers. These iodophors function to not only increase the iodine solubility but to reduce the level of free molecular iodine in solution and to provide a type of sustained release reservoir of elemental iodine. Iodophors are known using carriers of polymers such as polyvinylpyrrolidone, copolymers of N-vinyl lactams with other unsaturated monomers such as, but not limited to, acrylates and acrylamides, various polyether glycols including polyether-containing surfactants such as nonylphenolethoxylates and the like, polyvinyl alcohols, polycarboxylic acids such as polyacrylic acid, polyacrylamides, polysaccharides such as dextrose, and the like, and combinations thereof. A preferred group of iodophors include polymers such as a polyvinylpyrrolidone (PVP), a copolymer of N-vinyl lactam, a polyether glycol (PEG), a polyvinyl alcohol, a polyacrylamide, a polysaccharide, and combinations thereof. Also reported in U.S. Pat. No. 4,597,975 (Woodward et al.) are protonated amine oxide surfactant-triiodide complexes that are also suitable iodophors for use in the present invention. Various combinations of iodophores can be used in the compositions of the present invention.

A preferred iodophor is povidone-iodine. A particularly preferred iodophor can be obtained commercially as povidone-iodine USP, which is a complex of K30 polyvinylpyrrolidone, iodine, and iodide wherein the available iodine is present at about 9 wt-% to about 12 wt-%.

Preferably, the iodophor is present in the use compositions at a concentration of at least about 2.5 wt-%, and more preferably at least about 5 wt-%, and most preferably greater than 5 wt-%, based on the total weight of the antiseptic composition. To prevent the dried composition from becoming excessively water soluble, the concentration of iodophor in the use composition is preferably present at not more than about 15 wt-%, and more preferably not more than about 10 wt-%, based on the total weight of the antiseptic composition.

Since iodophors may vary in the amount of available iodine it is usually more convenient to describe the concentration in terms of the available iodine level. In the present invention, whether from iodine or an iodophor or a combination thereof, the available iodine concentration is preferably at least about 0.25 wt-%, and more preferably at least about 0.5 wt-%, based on the total weight of the antiseptic composition. The available iodine is preferably present at not more than about 1.5 wt-%, and preferably not more than about 1 wt-%, based on the total weight of the antiseptic composition.

The available iodine for most compositions may be determined by following the method in the United States Pharmacopeia Official Monographs for Povidone-Iodine, Assay for Available Iodine. Certain formulations may contain components that can interact with the method such as other anionic species. For this reason, the proper standards must be run to ensure accuracy, and solvent systems or reagents may need to be changed to ensure accuracy. One skilled in the art would appreciate these considerations.

Hydroxycarboxylic Acid Buffers

The compositions of the present invention are preferably buffered to prevent pH drift during storage. For example, it is well known that for iodine-containing systems it is important to maintain the pH at about 2 to about 6, and preferably at about 3 to about 5. As the pH is raised above about 6, the iodine can be rapidly converted to iodide, thus inactivating the antimicrobial effectiveness, if such is desired. Much below about a pH of about 2 and the composition may become irritating. In the compositions of the present invention, the pH is preferably adjusted to about 3.0 to about 4.5, and more preferably to about 3.5 to about 4.2.

While conventional compositions have included a buffer concentration of about 0.1 wt-% to about 2 wt-%, compositions of the present invention include certain hydroxycarboxylic acid buffers that can be used in much higher buffer concentrations. Preferably, the hydroxycarboxylic acid buffer is present in an amount of at least about 5 wt-%, and more preferably at least about 6 wt-%, based on the total weight of the antiseptic composition.

Surprisingly, these compositions (i.e., with a pH preferably adjusted to about 3.0 to about 4.5, and more preferably to about 3.5 to about 4.2, and a relatively high hydroxycarboxylic acid buffer concentration—at least about 5 wt-%, and more preferably at least about 6 wt-%) are substantially non-irritating to tissue (e.g., skin and mucosal tissue), as indicated by studies conducted by instilling aliquots (of use concentrations) into rabbit eyes. This is illustrated in the examples, which indicates that compositions of the present invention when tested according to the Rabbit Eye Irritation Test produce very little, if any, corneal opacity, with substantially complete return to normal (i.e., clear or having a Draize score of zero) in no greater than about 96 hours, and preferably no greater than about 72 hours. This indicates that the compositions would be very gentle for use on skin and mucosal tissue. This is very surprising since previous reports have indicated that high levels of alpha-hydroxy acids at an acidic pH can be irritating to the skin.

This level of buffer is particularly desirable for antiseptic compositions that include povidone-iodine (particularly povidone-iodine USP) as the antimicrobial agent. In these systems the level of rapid microbial kill increases significantly and for some systems in a linear fashion with the molar concentration of the hydroxycarboxylic acid.

Preferred hydroxycarboxylic acid buffers include one or more compounds represented by the formula:

$$R^1(CR^2OH)_n(CH_2)_m COOH$$

wherein: $R^1$ and $R^2$ are each independently H or a (C1-C8) alkyl group (saturated straight, branched, or cyclic group), a (C6-C12)aryl, or a (C6-C12)aralkyl or alkaryl group (saturated straight, branched, or cyclic alkyl group), wherein $R^1$ and $R^2$ may be optionally substituted with one or more carboxylic acid groups; m=0 or 1; and n=1-3, preferably, n=1-2.

It is particularly desirable that the buffers and other excipients that contain hydrocarbon groups are saturated or contain low levels of unsaturation to prevent iodine addition, which may deplete the iodine in the composition and/or produce toxic species. Preferably, the level of unsaturation in the composition is no greater than about 50 milliequivalents per liter (meq/L), more preferably, no greater than about 5 meq/L, and most preferably, no greater than about 0.5 meq/L unsaturation.

The hydroxycarboxylic acid buffers of the present invention include preferably beta- and alpha-hydroxy acids (BHAs, AHAs, respectively, collectively referred to as hydroxy acids (HAs)), salts thereof, lactones thereof, and/or derivatives thereof. These may include mono-, di-, and trifunctional carboxylic acids. Particularly preferred are HAs having 1 or 2 hydroxyl groups and 1 or 2 carboxylic acid groups. Suitable HAs include, but are not limited to, lactic acid, malic acid, citric acid, 2-hydroxybutanoic acid, 3-hydroxybutanoic acid, mandelic acid, gluconic acid, tartaric acid, salicylic acid, as well as derivatives thereof (e.g., compounds substituted with hydroxyls, phenyl groups, hydroxyphenyl groups, alkyl groups, halogens, as well as combinations thereof)). Preferred HAs include lactic acid, malic acid, and citric acid. These acids may be in D, L, or DL form and may be present as free acid, lactone, or salts thereof. Other suitable HAs are described in U.S. Pat. No. 5,665,776 (Yu et al.). The preferred HAs for use with iodine and in particular with povidone-iodine are lactic and malic acid. Various combinations of hydroxycarboxylic acids can be used if desired.

A hydroxycarboxylic acid buffer is preferably present in a molar concentration of at least about 0.3 molar, more preferably at least about 0.45 molar, and most preferably at least about 0.6 molar. For formulations where very rapid microbial kill on skin is desired the hydroxycarboxylic acid concentration is in excess of 0.7 molar.

Generally, the antimicrobial efficacy of povidone/iodine formulations is directly related to the molar concentration of hydroxycarboxylic acid buffer. With sufficiently high levels of hydroxycarboxylic acid buffer, the compositions are able to reduce the normal skin flora on a dry human skin site (typically, the back or abdomen) by an average of greater than or equal to 2 logs in only 2 minutes following a 30-second scrub, and preferably following a simple painting application (no scrubbing) where the site is painted 3 times when tested according to ASTM testing method E1173-93. This is demonstrated in the Examples Section.

Typically, the concentration of hydroxycarboxylic acid buffer in weight percent of the use composition is at least about 5 wt-% and often at least about 7 wt-%, based on the weight of the use composition. The concentration of hydroxycarboxylic acid buffer is preferably no greater than about 15 wt-%, more preferably no greater than about 10 wt-%, and most preferably no greater than about 5 wt-%, based on the weight of the use composition. It may also be convenient in some applications to supply concentrates that have much higher concentration of hydroxycarboxylic acid buffer but when diluted to the use concentration fall within the specified ranges.

High concentration of hydroxycarboxylic acid buffers would be expected to contribute to poor PSA-coated product adhesion especially over long wear times. In long wear time applications, moisture build-up from transpiration and perspiration in combination with external fluid exposure is believed to be the principle mode of failure. Incorporation of hydrophilic compounds usually results in premature adhesion failure. For example, incorporation of glycols such as glycerin and propylene glycol at levels as low as 3% significantly reduces the adhesion of PSA-coated products. With certain hydroxycarboxylic acid buffers (e.g., lactic acid, malic acid, and citric acid), however, surprisingly concentrations in excess of 5 wt-% and even as high as 10-13 wt-% still allow sufficient PSA-coated product (e.g., incise drape) adhesion.

Preferably, the ratio of hydroxycarboxylic acid ("HA") buffer (free acids, as well as lactones thereof, salts thereof, or derivatives thereof) to antimicrobial agent is at least about 4.0 grams HA buffer per gram available iodine, more preferably, at least about 6.5 grams HA buffer per gram available iodine, and most preferably, at least about 9.0 grams HA buffer per gram available iodine.

Vehicle

Suitable liquid vehicles for the antiseptic compositions of the present invention include water, optionally in combination with acetone or an alcohol, particularly a (C1-C4)alcohol (i.e., a lower alcohol) such as ethanol, 2-propanol, and n-propanol, and mixtures thereof. The preferred vehicle is injectable-grade water, i.e., USP grade "water for injection", however, other forms of purified water may be suitable such as distilled and deionized water.

For applications to in-tact skin, however, it may be desirable to include a lower alcohol such as ethanol, isopropanol, or n-propanol. These alcohols are well known to contribute to rapid microbial kill. For these applications the alcohol to water ratio is preferably at least about 60:40, and more preferably at least about 70:30, by weight. Addition of alcohol in these high concentrations will also decrease the dry time of the composition.

When a lower alcohol is used, incorporation of surfactants (as discussed in greater detail below) may or may not be necessary. In some cases elimination of the surfactant may allow for better adhesion of PSA-coated products over the dried film.

Particularly preferred antiseptic compositions include water and are substantially free (i.e., less than about 10 wt-%) of volatile organic solvents (i.e., those having a closed-cap flash point of greater than about 140° F. (60° C.)), such as acetone, lower alcohols, alkanes, volatile silicones, etc.

Aqueous formulations are preferred since these formulations are gentle to both skin and mucosal tissue and may even be suitable for use on open wounds as a wound cleanser. Furthermore, compositions containing organic solvents may also be flammable, which is typically a consideration in shipping and handling the product.

Preferred compositions of the present invention include less than about 5 wt-% volatile organic solvents, and more preferably less than about 3 wt-% volatile organic solvents, based on the total weight of the composition. These preferred aqueous compositions typically are nonflammable, having a closed-cup flash point of greater than about 140° F. (60° C.). The addition of lower alcohols (C1-C4) at less than about 4 wt-% may improve wetting of the compositions and yet maintain a flashpoint above about 140° F. (60° C.). Flashpoint is measured according to test method ASTM D3278-96.

Optional Film-Forming Polymers

It is particularly desirable to add one or more film-forming polymers to the antiseptic compositions to improve substantivity (e.g., resistance to wash off by blood and body fluid exposure), improve adhesion of PSA-coated products, and/or reduce the tack of the compositions. Preferred film-forming polymers of the antiseptic compositions of the present invention are substantive and resist removal by prolonged exposure to fluids such as water, saline, and body fluids, yet can be easily and gently removed without the need for organic solvents.

Preferred film-forming polymers have both hydrophilic and hydrophobic moieties. Particularly preferred film-forming polymers include relatively high levels of total hydrophobic monomers. The preferred polymers are relatively hydrophobic to provide good substantivity and prolonged adhesion of PSA-coated products. Particularly preferred polymers are formed using a hydrophobic monomer level of at least about 50 wt-%, and often as high as 80 wt-%, based on the total weight of the polymerizable composition (and preferably, based on the total weight of the polymer). Various combinations of hydrophobic monomers can be used if desired.

Examples of suitable hydrophobic and hydrophilic monomers are described in Applicants' Assignee's U.S. Pat. No. 6,838,078.

The film-forming polymers may be nonionic, anionic, or cationic. They may also have pressure sensitive adhesive properties. These include both synthetic and natural polymers as well as derivatives of natural polymers. Preferred film-forming polymers are cationic.

Surprisingly, the solubility and stability of cationic film-forming polymers are not affected detrimentally by the presence of multifunctional carboxylic acid containing hydroxyacids such as citric acid, malic acid, tartaric acid, and the like. This is particularly surprising since it would be expected that adding these acids into compositions containing cationic polymers at very high concentrations would result in precipitation of the polymer due, for example, to ionic crosslinking.

Preferred film-forming polymers are cationic polymers, particularly those that include side-chain functional amine groups. Examples of such groups include protonated tertiary amines, quaternary amines, amine oxides, and combinations thereof. Preferred such polymers are described in Applicants' Assignee's U.S. Pat. No. 6,838,078.

Preferred film-forming polymers are vinyl polymers prepared from amine group-containing monomers. Preferably, the vinyl polymers have a Tg of at least about 30° C., and more preferably at least about 50° C. One method of measuring the Tg of a polymer may involve the utilization of a Differential Scanning Calorimeter (DSC, e.g., the PYRIS 7-Series Thermal Analyzer, Perkin-Elmer, Shelton, Conn.) in the range of −100° C. to +100° C. at a rate of 20° C. per minute.

For certain preferred film-forming polymers, the amine group-containing monomers can be used to prepare the film-forming polymers in an amount of at least about 15 wt-%, more preferably at least about 20 wt-%, even more preferably at least about 25 wt-%, and most preferably at least about 30 wt-%, based on the total weight of the polymerizable composition (and preferably, based on the total weight of the polymer). The amine group-containing monomers used to prepare the film-forming polymers are typically used in an amount of no greater than about 70 wt-%, preferably no more greater than about 65 wt-%, more preferably no greater than about 60 wt-%, and most preferably no greater than about 55 wt-%, based on the total weight of the polymerizable composition (and preferably, based on the total weight of the polymer).

The equivalent weight of the amine group contained in the polymer is preferably at least about 300, more preferably at least about 350, even more preferably at least about 400, and most preferably at least about 500, grams polymer per equivalent of amine group. The equivalent weight of the amine group contained in the polymer is preferably no greater than about 3000, more preferably no greater than about 1500, even more preferably no greater than about 1200, and most preferably no greater than about 950, grams polymer per equivalent of amine group.

Examples of film-forming polymers that are PSAs at room temperature include those based on side-chain functional amine group monomers in combination with long chain alkyl acrylic polymers and optionally other hydrophilic monomers. For example, a particularly effective polymer that is a PSA includes 80% 2-ethylhexylacrylate and 20% trimethylaminoethyl methacrylate chloride, based on the total weight of the polymerizable composition (and preferably, based on the total weight of the polymer). Another PSA polymer in this class includes 75% 2-ethylhexyl acrylate, 25% trimethylaminoethyl methacrylate chloride, and 5% of a methoxy polyethylene glycol (about 9 ethyleneoxy units) monoacrylate, which is commercially available from Shin-Nakamura Chemicals, Wakayama City, Japan under the trade designation AM-90G.

Preferably the viscosity of a composition of the present invention is no greater than about 1000 cps when measured at 23° C. using a Brookfield RVT ROTOVISCO viscometer. Therefore, the film-forming polymers of the present invention preferably have an inherent viscosity of no greater than about 0.75 and preferably no greater than about 0.5 as measured in tetrahydrofuran according to the method in the Examples Section. In order to ensure sufficient substantivity, however, the inherent viscosity of the film-forming polymer is preferably at least about 0.1, as measured in tetrahydrofuran according to the method in the Examples Section.

The molecular weight of the polymers is also preferably kept low in order to maintain a low viscosity composition. Preferably, the molecular weight of the polymers is generally no greater than about 350,000 Daltons, more preferably no greater than about 250,000 Daltons, even more preferably no greater than about 150,000 Daltons, and most preferably no greater than about 100,000 Daltons.

One or more film-forming polymers, preferably substantive film-forming polymers, are present in the antiseptic composition in a total amount of at least about 2 wt-%, preferably at least about 3 wt-%, and more preferably at least about 5 wt-%, based on the total weight of antiseptic composition. One or more film-forming polymers, preferably substantive film-forming polymers, are present in the antiseptic composition in a total amount of no greater than about 10 wt-%, and more preferably no greater than about 8 wt-%, based on the total weight of antiseptic composition. The optional film-forming polymers are preferably present in an amount to provide a substantive composition.

Higher concentrations of the film-forming polymer appear to promote adhesion of PSA-coated products. In certain compositions, however, higher concentrations may not be possible due to instability especially when exposed to temperatures above 50° C.

Preferably, in order to ensure adequate substantivity the weight ratio of film-forming polymer to hydroxycarboxylic acid is at least about 0.25:1, preferably at least 0.35:1, more preferably at least about 0.5:1, and most preferably at least about 0.70:1.

Optional Surfactants

It is particularly desirable when formulating with a film-forming polymer to include one or more surfactants to enhance solubility and stability of the polymer in the composition. In addition, surfactants help the compositions to wet the skin and ensure a smooth uniform coating. It is particularly important to provide a thin uniform coating that has complete coverage to ensure easy error-free application that will dry rapidly due to the thinness of the coating. In addition, certain surfactants may increase the antimicrobial activity.

If used, one or more surfactants are generally added to the antiseptic compositions of the present invention in an amount of at least about 0.5 wt-%, based on the total weight of the composition. Preferably, one or more surfactants are generally added to the antiseptic compositions of the present invention in an amount of no greater than about 10 wt-%, more preferably no greater than about 7 wt-%, even more preferably no greater than about 5 wt-%, and most preferably no greater than about 3 wt-%, based on the total weight of the composition. Too little surfactant results in an unstable composition especially upon exposure to elevated temperatures. Too much surfactant can undermine the substantivity of the dried composition on skin. For this reason, the surfactant level is generally chosen as slightly above the minimum level of total surfactant required to ensure stability at 50° C.

Furthermore, it is preferred to use surfactants having low inorganic salt impurities such as sodium chloride, sodium sulfate, etc. Preferably, such salt content should be sufficiently low such that a 20% solution of the surfactant in water has a conductivity of less than about 100 micromhos/cm, more preferably less than about 85 micromhos/cm, and most preferably less than about 75 micromhos/cm.

The following types of surfactants can be used if desired:

a. Nonionic Surfactants. Particularly useful surfactants are nonionic surfactants. It has been found that polyalkoxylated, and in particular polyethoxylated, nonionic surfactants can stabilize the film-forming polymers of the present invention in aqueous solutions particularly well. In general, useful polyalkoxylated nonionic surfactants preferably have a hydrophile/lipophile balance (HLB) of at least about 14, and more preferably at least about 16. Useful polyalkoxylated nonionic surfactants preferably have an HLB of no greater than about 19. When using combinations of nonionic surfactants a weight average HLB is used to determine the HLB of the nonionic surfactant system. As used herein, the HLB is defined as one-fifth the weight percentage of ethylene oxide segments in the surfactant molecule.

Surfactants of the nonionic type that have been particularly useful include:

1. Polyethylene oxide extended sorbitan monoalkylates (i.e., Polysorbates). In particular, a Polysorbate 20 commercially available as NIKKOL TL-10 (from Barret Products) is very effective.

2. Polyalkoxylated alkanols. Surfactants such as those commercially available under the trade designation BRIJ from ICI Specialty Chemicals, Wilmington, Del. having an HLB of at least about 14 have proven useful. In particular, BRIJ 78 and BRIJ 700, which are stearyl alcohol ethoxylates having 20 and 100 moles of polyethylene oxide, respectively, have proven very useful. Also useful is a ceteareth 55, which is commercially available under the trade designation PLU-RAFAC A-39 from BASF Corp., Performance Chemicals Div., Mt. Olive, N.J.

3. Polyalkoxylated alkylphenols. Useful surfactants of this type include polyethoxylated octyl or nonyl phenols having HLB values of at least about 14, which are commercially available under the trade designations ICONOL and TRI-TON, from BASF Corp., Performance Chemicals Div., Mt. Olive, N.J. and Union Carbide Corp., Danbury, Conn., respectively. Examples include TRITON X100 (an octyl phenol having 15 moles of ethylene oxide available from Union Carbide Corp., Danbury, Conn.) and ICONOL NP70 and NP40 (nonyl phenol having 40 and 70 moles of ethylene oxide units, respectively, available from BASF Corp., Performance Chemicals Div., Mt. Olive, N.J.). Sulfated and phosphated derivatives of these surfactants are also useful. Examples of such derivatives include ammonium nonoxynol-4-sulfate, which is commercially available under the trade designation RHODAPEX CO-436 from Rhodia, Dayton, N.J.

4. Polaxamers. Surfactants based on block copolymers of ethylene oxide (EO) and propylene oxide (PO) have been shown to be effective at stabilizing the film-forming polymers of the present invention and provide good wetting. Both EO-PO-EO blocks and PO-EO-PO blocks are expected to work well as long as the HLB is at least about 14, and preferably at least about 16. Such surfactants are commercially available under the trade designations PLURONIC and TETRONIC from BASF Corp., Performance Chemicals Div., Mt. Olive, N.J. It is noted that the PLURONIC surfactants from BASF have reported HLB values that are calculated differently than described above. In such situation, the HLB values reported by BASF should be used. For example, preferred PLURONIC surfactants are L-64 and F-127, which have HLBs of 15 and 22, respectively. Although the PLURONIC surfactants are quite effective at stabilizing the compositions of the present invention and are quite effective with iodine as the active agent, they may reduce the antimicrobial activity of compositions using povidone-iodine as the active agent.

5. Polyalkoxylated esters. Polyalkoxylated glycols such as ethylene glycol, propylene glycol, glycerol, and the like may be partially or completely esterified, i.e., one or more alcohols may be esterified, with a (C8-C22)alkyl carboxylic acid. Such polyethoxylated esters having an HLB of at least about 14, and preferably at least about 16, are suitable for use in compositions of the present invention.

6. Alkyl Polyglucosides. Alkyl polyglucosides, such as those described in U.S. Pat. No. 5,951,993 (Scholz et al.), starting at column 9, line 44, are compatible with the film-forming polymers of the present invention and may contribute to polymer stability. Examples include glucopon 425, which has a (C8-C16)alkyl chain length with an average chain length of 10.3 carbons and 1-4 glucose units.

b. Amphoteric Surfactants. Surfactants of the amphoteric type include surfactants having tertiary amine groups which may be protonated as well as quaternary amine containing zwitterionic surfactants. Those that have been particularly useful include:

1. Ammonium Carboxylate Amphoterics. This class of surfactants can be represented by the following formula:

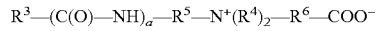

$$R^3-(C(O)-NH)_a-R^5-N^+(R^4)_2-R^6-COO^-$$

wherein: $a=0$ or 1; $R^3$ is a (C7-C21)alkyl group (saturated straight, branched, or cyclic group), a (C6-C22)aryl group, or a (C6-C22)aralkyl or alkaryl group (saturated straight, branched, or cyclic alkyl group), wherein $R^3$ may be optionally substituted with one or more N, O, or S atoms, or one or more hydroxyl, carboxyl, amide, or amine groups; $R^4$ is H or a (C1-C8)alkyl group (saturated straight, branched, or cyclic group), wherein $R^4$ may be optionally substituted with one or more N, O, or S atoms, or one or more hydroxyl, carboxyl, amine groups, a (C6-C9)aryl group, or a (C6-C9)aralkyl or alkaryl group; and $R^5$ and $R^6$ are each independently a (C1-C10)alkylene group that may be the same or different and may be optionally substituted with one or more N, O, or S atoms, or one or more hydroxyl or amine groups.

More preferably, in the formula above, $R^3$ is a (C1-C16) alkyl group, $R^4$ is a (C1-C2)alkyl group preferably substituted with a methyl or benzyl group and most preferably with a methyl group. When $R^4$ is H it is understood that the surfactant at higher pH values could exist as a tertiary amine with a cationic counterion such as Na, K, Li, or a quaternary amine group.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

2. Ammonium Sulfonate Amphoterics. This class of amphoteric surfactants are often referred to as "sultaines" or "sulfobetaines" and can be represented by the following formula

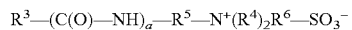

wherein $R^3$-$R^6$ and "a" are define above. Examples include cocamidopropylhydroxysultaine (commercially available as MACKAM 50-SB from McIntyre Group Ltd.).

c. Anionic Surfactants. Surfactants of the anionic type that have been particularly useful include:

1. Sultanates and Sulfates. Suitable anionic surfactants include sulfonates and sulfates such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates and the like. Many of these can be represented by the formulas:

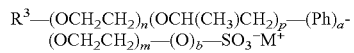

and

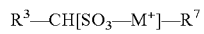

wherein: a and b=0 or 1; n, p, m=0-100 (preferably 0-40, and more preferably 0-20); $R^3$ is defined as above; $R^7$ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as Na, K, Li, ammonium, a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. Preferably for this class, $R^3$ comprises an alkylamide group such as $R^8$—C(O)N(CH$_3$)CH$_2$CH$_2$— as well as ester groups such as —OC(O)—CH$_2$— wherein $R^8$ is a (C8-C22)alkyl group (saturated branched, straight, or cyclic group).

Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17)secondary alkane sulfonates (alpha-olefin sulfonates) available from Clariant Corp., Charlotte, N.C.; methyl-2-sulfoalkyl esters such as sodium methyl-2-sulfo (C12-16)ester and disodium 2-sulfo(C12-C16)fatty acid available from Stepan Company under the trade designation ALPHASTE PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company.

2. Phosphates and Phosponates. Suitable anionic surfactants also include phosphates such as alkyl phosphates, alkylether phosphates, aralkylphosphates, and aralkylether phosphates. Many may be represented by the formula:

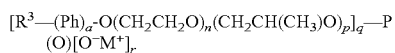

where: Ph, $R^3$, a, n, p, and M are defined above; r is 0-2; and q=1-3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement.

Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J.

3. Amine Oxides. Suitable anionic surfactants also include amine oxides including alkyl and alkylamidoalkyldialkylamine oxides of the following formula:

wherein $R^3$ is defined above and each $R^3$ may be the same or different.

Optionally, the $R^3$ groups can be joined to form a heterocyclic ring with the nitrogen to form surfactants such as amine oxides of alkyl morpholine, alkyl piperazine, and the like. Preferably two $R^3$ groups are methyl and one $R^3$ group is a (C12-C16)alkyl or alkylamidopropyl group.

Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company.

Combinations of various surfactants can be used if desired. For example, nonionic surfactants in combination with certain anionic surfactants described above can be used for certain advantage. For example, one preferred surfactant system is based on a combination of a polysorbate and a polyethoxylated alkyl alcohol (Polysorbate 20+steareth-100).

Certain preferred anionic surfactants include a polyalkoxylate group. These include the sulfonates, sulfates, phosphates, and phosphonates.

For certain embodiments, it is desirable to select one or more surfactants that associate or potentially associate with other components in the composition after dry down may be tolerated better. For example, certain anionic surfactants such as methyl-2-sulfoalkyl esters (e.g., sodium methyl-2-sulfo (C12-16) ester and disodium 2-sulfo(C12-C16)fatty acid available from Stepan Company under the trade designation ALPHASTEP PC-48) in combination with polyamine oxide film-forming polymers appear to increase the substantivity of a dried film of the antiseptic composition and adhesion of PSA-coated products. Certain of the sulfate and sulfonate containing surfactants also appear to significantly reduce dry times. The mechanism for this is not clear. While not intending to be bound by theory these surfactants may associate with cationic amine groups on film-forming polymers forming a more hydrophobic complex during dry down. Sulfates and sulfonates, phosphates and phosphonates, as well as the sulfobetaine type surfactants have been shown to reduce the dry time significantly.

Other Optional Ingredients

In addition to film-forming polymers and surfactants, a variety of other ingredients may be added to the antiseptic compositions of the present invention for desired effect. These include, but are not limited to, skin emollients and humectants such as those described in U.S. Pat. No. 5,951, 993 (Scholz et al.), fragrances, colorants, tackifiers, plasticizers, etc.

Other antimicrobial agents and preservatives may be included as long as they are compatible with the compositions. These include, but are not limited to, chlorhexidine salts such as chlorhexidine gluconate (CHG), parachlorometaxylenol (PCMX), triclosan, hexachlorophene, fatty acid monoesters of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants and polymers that include a (C12-C22)hydrophobe and a quaternary ammonium group, polycationic amines such as polyhexamethylene biguanide, quaternary silanes, silver, silver salts such as silver chloride, silver oxide and silver sulfadiazine, methyl, ethyl, propyl and butyl parabens, octenidene, and the like, as well as combinations thereof.

Formulation of Preferred Embodiments with Low or No Tack

The preferred skin antiseptics of the present invention provide low tack or nontacky dry films, which can be removed with a water-soaked fabric such as a towel or simple gauze. Low tack is desirable to prevent skin from attaching together, such as beneath a breast or in a skin-fold.

The tack can be measured by spreading a film of about 4 milligrams (mg) of the composition per square centimeter of skin on an inner forearm and allowing this to dry thoroughly. A dry thumb (washed with IVORY bar soap and dried thoroughly before testing) is then pressed onto the dry film and immediately removed. In preferred formulations there is essentially no perception of tack similar to the performance of a 10% povidone-iodine solution (such as that commercially available under the trade designation BETADINE Surgical Solution from Purdue Frederick Company, Norwalk Conn.). The most preferred preps can also be evaluated by pressing a facial tissue such as a KLEENEX brand tissue available from Kimberly-Clark, Roswell, Ga. over the prep and releasing. The tissue should fall off under its own weight. Due to the variability in skin types this should be done with multiple subjects painted with the test compositions and multiple evaluators.

Tack of the dried composition can be due to various factors such as the Tg of the film-forming substantive polymer, and the level of hydrophilic additives (e.g., glycols, certain low molecular weight organic acids, certain surfactants, antimicrobial agents, and the like) in the formulation which may plasticize the film. For example, certain iodophors such as PEG- or PVP-based iodophors can be plasticized by low molecular weight hydrophilic compounds. These compounds can further retain water in the films and contribute to tack.

Despite their very hydrophilic nature, however, the preferred organic acid buffers of the present invention do not contribute significantly to higher tack. While not intending to be bound by theory this may be due to hydrogen bond association between the carboxylic acid and the pyrrolidone ring carbonyl or the ether oxygen of the iodophor.

The tack of the dried compositions can be particularly high if the formulations contain film-forming substantive polymers that are pressure sensitive adhesives at skin temperature. For such compositions, as well as others that may be tacky, certain excipients that can be added to reduce the tack. For example, the tack can be controlled by the addition of: high Tg polymers; certain polyfunctional acids; and certain surfactants.

Certain high Tg polymers, such as those having a Tg of at least about 30° C., preferably at least about 50° C., more preferably at least about 55° C., and most preferably at least about 70° C., can reduce the tack of a composition of the present invention significantly. Suitable such polymers include polyvinyl alcohols. A preferred high Tg polymer (Tg reported as 75-80° C.) for reducing tack is hydrolyzed polyvinyl alcohol (PVA) having a degree of hydrolysis greater than about 97%. Such a material is commercially available under the trade designation CELVOL 305 as a 98-98.8% hydrolyzed PVA from Celanese Ltd., Dallas, Tex. This material is particularly desirable because it is of a relatively low molecular weight having a viscosity in water at 4% at 23° C. of only 4.5-5.5 cps. Also, although it is rather hydrophilic, hydrolyzed PVA does not detrimentally affect the substantivity of a dried composition of the present invention. While not being bound by theory, it is believed that the high degree of hydrolysis contributes to low tack without detrimentally affecting substantivity due to the fact that these polymers are not cold water soluble and thus once dried may resist going back into solution.

It has also been found that certain polyfunctional acids can dramatically reduce the tack of a composition of the present invention. For example, malic acid may reduce the tack of a formulation compared a similar formulation having lactic acid in an equivalent molar amount. Molecules having 3 or more carboxylic acids are particularly effective in reducing the tack of certain compositions. For example, certain compositions having PSA film-forming polymers that include quaternary ammonium side-chain functional group monomers and long chain alkyl group monomers can be detackifed by the addition of citric acid. Formulations that are aggressively tacky can be modified to have very low tack at 3% citric acid and essentially no tack at 5% citric acid. While not being bound by theory, it is believed that these polyfunctional acids may be forming ionic crosslinks with the quaternary ammonium groups on the film-forming polymer.

Certain surfactants can reduce the tack of compositions of the present invention. Particularly effective are silicone copolyol surfactants, which are surfactants based on polydialkylsiloxanes having pendant side-chains of polyalkyleneglycols. Many of these surfactants dramatically reduce the tack of the formulations, however, most of these surfactants also inhibited the adhesion of PSA-coated products over the dry prep. Certain low molecular weight silicone copolyols, such as that commercially available under the trade designation MASIL SF-19CG from PPG Industries, are able to reduce the tack of the compositions and yet not significantly inhibit the adhesion of PSA-coated products.

Also, the tack of the compositions can be reduced by using polymers that are not PSA in nature. These polymers generally have a glass transition temperature of greater than about 30° C. For example, polymers having higher amounts of short chain alkyl group tend to have higher glass transition temperatures and thus can yield substantially nontacky compositions. For example, one class of preferred polymers is based on at least a ternary combination of side-chain amine group functional monomers copolymerized with both short chain alkyl (meth)acrylate hydrophobic monomers and long chain alkyl (meth)acrylate hydrophobic monomers.

In particular, the following two groups of polymers are highly desirable:

Polymer System A:

| | | Weight % | |
|---|---|---|---|
| Monomer | Class | Range | Preferred Range |
| Dimethylamine oxide methacrylate | amine group | 25-60 | 35-55 |
| Isobutylmethacrylate | long chain alkyl | 10-30 | 10-25 |
| Methylmethacrylate | short chain alkyl | 10-45 | 10-25 |
| (C12-C18)alkylmethacrylate | long chain alkyl | 0-30 | 5-15 |

Preparation of the Amine Oxide Containing Polymers is Described Later in the Example Section, however, it should be noted that the above percentages are given on a basis that all tertiary amine is converted to amine oxide. This may not always be the case. In preferred polymers at least about 50%, more preferably at least about 60%, and most preferably at least about 70%, of the tertiary amine is converted to the amine oxide. The most preferred polymer of this class is that commercially available under the trade designation DIAFORMER Z-731 from Clariant Corp., Mt Holly, N.C.

Polymer System B:

| | | Weight % | |
|---|---|---|---|
| Monomer | Class | Range | Preferred Range |
| Trimethylaminoethyl acrylate chloride | amine group | 20-50 | 35-45 |
| Methylmethacrylate | short chain alkyl | 10-55 | 40-50 |
| C12-C18 alkyl methacrylate | long chain alkyl | 0-30 | 2-15 |
| Butyl acrylate | long chain alkyl | 0-80 | 5-20 |

The most preferred polymer of this class includes 40% trimethylaminoethyl methacrylate chloride, 45% methylmethacrylate, 5% lauryl acrylate, and 10% butyl acrylate where all percentages are weight percent of the polymerizable composition.

Application and Use

The compositions of the present invention are preferably supplied in the concentration intended for use but may be prepared as concentrates that are diluted prior to use. For example, concentrates requiring dilution ratios of 0.5:1 to 3:1 parts water to concentrate are contemplated. The higher limit of the concentrate is limited by the solubility and compatibility of the various components at higher concentrations.

The compositions of the present invention may be applied to the skin using any suitable means. Ordinarily an absorbent of some type such as gauze, foam sponges, non-woven fabrics, cotton fabrics, cotton swabs or balls, and the like, are soaked with the composition which is used to wipe the composition over the intended site. With very high activity compositions having exceptional wetting properties (e.g., higher alcohol content formulations), a single stroke prep may be all that is necessary. In most cases, however, it is believed that it helps to wipe the soaked absorbent across the skin several times, preferably in various directions, in order to thoroughly wet the skin and ensure good coverage into the finer details of the skin. In general, however, extensive scrubbing is not called for as is recommended by prior art products due to the enhanced activity resulting from the high concentration of organic buffer. For example, the manufacturer of BETADINE Surgical Scrub (Purdue Frederick Company, Norwalk, Conn.) specifies that the user scrub thoroughly for 5 minutes. The compositions of the present invention require scrubbing for less than about 60 seconds, preferably less than about 45 seconds, and most preferably for less than about 30 seconds, followed by a 2-minute wait without blotting.

In order to maintain strict asepsis, however, the applier of a preoperative patient skin prep should start at the proposed site of the incision and work outward never returning to the incision site with a "dirty" applicator. The most preferred compositions of the present invention can be wiped on the skin in a simple overlapping motion taking care to cover each spot at least two or three times as the user works outward such that essentially no scrubbing is required.

For some applications it may be desirable to place a PSA-coated article over a film of the dried composition. For example, if the composition is used as a skin prep for precatheterization it is generally recommended to cover the puncture site to maintain sterility. This is generally done by placing gauze and tape or a wound dressing over the puncture site and on top of the dried composition. These products are PSA-coated articles and adhesion to the dried composition is important to maintain asepsis. Similarly, if the compositions are used as preoperative skin preps it is often desirable to place a PSA-coated drape (a so-called incise drape) over the dried prep. The purpose of the adhesive-coated drape is to seal off the nonsterile skin and provide the surgeon with a sterile surface. The surgeon makes the incision through this drape. Thus, it is important that the drape adhere to the dried composition and resist lift during the procedure.

In order to achieve good initial and prolonged adhesion of PSA-coated products such as tapes, wound dressings, incise drapes, and the like, it is highly desirable and preferable to formulate compositions with the following characteristics: a relatively low surfactant concentration (preferably no greater than about 10 wt-%, more preferably no greater than about 7 wt-%, even more preferably no greater than about 5 wt-%, and most preferably no greater than about 4 wt-%); one or more surfactants that associate or potentially associate with other components in the composition during and/or after dry down; one or more film-forming polymers with higher content of hydrophobic monomer; a relatively high film-forming polymer concentration (preferably at least about 2 wt-%, more preferably at least about 3 wt-%, and most preferably at least 5 wt-%); and a relatively low hydroxycarboxylic acid concentration (preferably no greater than about 15 wt-%, more preferably no greater than a bout 12.5 wt-%, and most preferably no greater than about 10 wt-%).

Medical tapes and dressings that adhere particularly well to the compositions of the present invention when dry include those utilizing acrylate-based pressure sensitive adhesives, block copolymer-based pressure sensitive adhesives (e.g., adhesives based on KRATON polymers commercially available from Kraton Polymers, Houston, Tex.), and rubber-based pressure sensitive adhesives. Examples include tapes and dressings commercially available from 3M Company, St. Paul, Minn., under the trade designations TRANSPORE, BLENDERM, STERI-STRIPS, MICROPORE, TEGADERM, STERIDRAPE, and IOBAN 2.

A pressure sensitive adhesive tape applied over the dried compositions of the present invention on skin preferably adheres at a level of at least about 50% of the level of adhesion of the pressure sensitive adhesive tape applied over dried povidone-iodine solutions (specifically BETADINE Surgical Scrub (7.5% povidone-iodine solution) and BETADINE Surgical Solution (10% povidone-iodine solution), both of which are commercially available from Purdue Frederick Company, Norwalk, Conn.). This can be measured by applying a thin uniform amount of the test composition to skin as described in the Examples Section, allowing the film to dry, applying the PSA-coated tape (such as 0.5 inch (1.27 cm) wide samples of 3M IOBAN 2 Antimicrobial Incise Drape (3M Company, St. Paul, Minn.)), and rolling with a 4.5-pound (2.1-kg), 2-inch (5.1-cm) wide roller. After waiting at least 1 minute, and preferably 5 minutes, the PSA-coated tape is removed at a peel angle of 180 degrees at a speed of 12 inches/minute (30.5 cm/minute). Due to the variability in skin types, a statistically relevant sample is employed, which is typically at least 8 subjects where at least 2 strips are applied to the backs of each subject.

The compositions of this invention, if applied in a thin film to the skin and allowed to dry, preferably allow immediate adhesion of medical adhesive products. That is, typically and preferably, within about 3 minutes of application of a thin film (or once the composition is dry to the touch), a PSA-coated product can be applied over the composition that will exhibit good adhesion in as little as about 5 minutes, preferably in as little as about 120 seconds, and most preferably in as little as about 60 seconds. Furthermore the adhesion is maintained for at least several hours after application.

For the present invention, the principal mode of failure of PSA-coated products, such as incise drapes, over dried skin preps is primarily exposure to moisture. Moisture that can dissolve part or all of the composition and contribute to lift may come from patient transpiration, perspiration, or from external sources such as surgical irrigation fluid, blood, catheter related edema and fluid, and the like.

EXAMPLES

The objects, features, and advantages of the present invention illustrated in the following examples, which incorporate particular materials and amounts, should not be construed to unduly limit this invention. All materials are commercially available unless otherwise stated or apparent. All parts, percentages, ratios, etc., in the examples are by weight unless otherwise indicated.

GLOSSARY

| | | |
|---|---|---|
| EHA | 2-ethylhexyl acrylate | BASF Corporation, Mt. Olive, NJ |
| LMA | lauryl methacrylate: SR313B | Sartomer, Exton, PA |
| SMA | stearyl methacrylate | Rohm and Haas, Philadelphia, PA |
| BA | butyl acrylate | Hoechst Celanese, Dallas, TX and ICI, Wilmington, DE |
| IBMA | isobutyl methacrylate | Monomer-Polymer & Dajac Lab, Inc., Feasterville, PA |
| DMAEAMC | dimethylaminoethyl acrylate methyl chloride quaternary salt (AGEFLEX FA1Q80MC); also referred to as trimethylaminoethyl methacrylate chloride salt 80% aqueous solution | Ciba Specialty Chemicals, Woodbridge, NJ |
| DMAEMA | dimethylaminoethyl methacrylate | Ciba Specialty Chemicals, Woodbridge, NJ |

GLOSSARY -continued

| | | |
|---|---|---|
| DMAEA | dimethylaminoethyl acrylate (AGEFLEX FA1) | Ciba Specialty Chem., Woodbridge, NJ |
| AM-90G | methoxy(polyethylene oxide) acrylate (approximately 450 MW) | Shin-Nakamura Chemicals, Wakayama City, Japan |
| MMA | methyl methacrylate | ICI |
| EtOH | ethanol SDA-3A, anhydrous | Eastman |
| EtOH | ethanol N-190 | Worum Chemicals, Minneapolis, MN |
| $H_2O_2$ | hydrogen peroxide, 50% aqueous solution | Sigma-Aldrich Fine Chemicals, Inc., St. Louis, MO |
| VAZO 67 | 2,2'-azobis (2-methylbutanenitrile) | E. I. du Pont de Nemours and Company, Wilmington, DE |
| Ascorbic Acid | ascorbic acid, vitamin C | Amend Drug & Chemical Co. |
| NaOH | sodium hydroxide | Sigma-Aldrich Fine Chemicals, Inc. |
| D-C Additive 62 | Dow-Corning Additive 62 defoamer | Dow-Corning, Midland, MI |
| TBHP | t-butyl hydroperoxide, 70% in water | Arco Chemicals |
| SFS | sodium formaldehyde sulfoxylate hydrate | Fluka |
| PLURONIC | PLURONIC block copolymer of poly(ethylene oxide) and poly(propylene oxide) | BASF Corporation |
| TBA | tertiary buty alcohol | Sigma-Aldrich Fine Chemicals |
| PVP-I | povidone-iodine USP | BASF Corporation |
| POLYSTEP B22 | Ammonium laureth 12 sulfate | Stepan Company, Northfield, IL |
| LA | L lactic acid, High Pure 88, USP | Purac America, Lincolnshire IL |
| MLA | DL malic acid | Universal Preserv-a-Chem, Edison, NJ |
| SILWET L-7614 | silicone copolyol | Witco Corporation, Greenwich, CT |
| DIAFORMER Z711, Z712, Z731, Z751 | aminoxide side-chain group acrylate | Clariant Corporation, Charlotte, NC |
| CELVOL 103, 305, 321 | 98-98.8% hydrolyzed polyvinyl alcohol | Celanese Ltd., Dallas, TX |
| CELVOL 502, 523 | 88% hydrolyzed polyvinyl alcohol | Celanese Ltd., Dallas, TX |
| MACKAM CB-35 | coco betaine | McIntyre Group Ltd., University Park, IL |
| THF | Tetrahydrofuran | Sigma-Aldrich Fine Chemicals |
| DI water | deionized water | |
| CA | citric acid | Universal Preserv-a-Chem, Edison, NJ |
| MDA | mandelic acid | Sigma-Aldrich Fine Chemicals |
| MMB | MMB glycol | CBC (America) Corp. New York, NY |
| TL10 | NIKKOL TL-10 | Barnet Products Corp., Englewood Cliffs, NJ |
| | TWEEN 20 | ICI |
| | BRIJ 700 | ICI |
| PLURAFAC A39 | ceteareth 55 | BASF |
| SURFONIC N-150 | nonylphenolethoxylate having an HLB of 15 | Huntsman Corp., Austin TX |

Test Protocols

Inherent Viscosity (IV)

The inherent viscosity of a polymer is measured in accordance with the protocol described by Fred Billmeyer, Jr. at pages 84-85 of the textbook entitled "Textbook of Polymer Science," Second Edition, published by Wiley-Interscience (1971). Briefly, solution viscosity is measured by comparing the efflux time (t) required for a specified volume of polymer solution to flow through a capillary tube with the corresponding efflux time ($t_0$) for the solvent. The measured variables t, $t_0$, and solute concentration (c) are then used to calculate inherent viscosity (also know as Logarithmic Viscosity) using the equation:

$$\eta = (\ln t/t_0)/c$$

For the examples of the present invention, IV was determined as a 0.15 to 0.50 weight percent solution of the film-forming polymer in tetrahydrofuran (THF). Amine oxide-containing polymers are not soluble in THF alone and thus are measured at a 0.15-0.5 weight percent solution in 50/50 THF/methanol by weight.

Molecular Weight Measurement

The polymer is diluted to 5 milligrams per milliliter (mg/mL) in THF and filtered with a 0.45 micron (i.e., micrometer) membrane; Mobile Phase: THF; Flow Rate: 1.0 milliliter per minute (mL/min); Detector: Waters 410 Refractive Index; Columns: UltraStyragel-6, 30×7.8 millimeters (mm) each; Standards: Polystyrene, narrow dispersity; ranging $7.5 \times 10^6$–580 molecular weight of polystyrene.

Human Skin Antimicrobial Activity

Many of the compositions were checked for antimicrobial activity in a method similar to ASTM testing method E-1173-93 Standard Test for Evaluation of a Pre-operative Skin Preparation except that the compositions were applied to the backs (considered a "dry" site) of healthy volunteers and the baseline bacterial flora counts as put forth in section 7.1 of the ASTM method were not as high. Preps were always compared to the 2-step application of BETADINE Surgical Scrub (7.5% povidone-iondine, Purdue Frederick Company, Norwalk, Conn.) and BETADINE Surgical Solution (10% povidone-iodine "paint", Purdue Frederick Company, Norwalk, Conn.) per the manufacturer's instructions. All studies were randomized block designs. On the Study Day, two samples for baseline microbial counts were taken, one from the upper back and one from the lower back, on opposite sides of the spine. The test formulations and the control were randomized on the back-usually four across the upper back and four across the lower back. The residual bacteria were sampled from all sites 2.0 minutes after completion of application. All test samples were applied using sterile gauze saturated with the test composition (fully wet and dripping) applied in one of two ways. In one method an approximately 2×2 inch (5.1 cm×5.1 cm) area was "scrubbed" for 30 seconds using moderate pressure. In a second method the prep was applied by simply painting the site with moderate pressure 3 times in a continuous motion without stopping. BETADINE Surgical Scrub and BETADINE Surgical Solution were applied following manufacturer's directions. Briefly, BETADINE Surgical Scrub was applied with saturated gauze and scrubbed for 5 minutes, wiped off; and the BETADINE Surgical Solution applied in an outward spiral from center. The compositions of the invention, therefore, had a much shorter time to kill than did the BETADINE scrub and paint procedure. A minimum of 8 subjects were used in accordance with sections 8.2-8.3 of ASTM testing method E1173. All subjects refrained from using antimicrobial products for a minimum of 2 weeks. The average log reduction from baseline was determined for each composition. If multiple sites were run the log reduction for each site was determined Results are reported in average log reductions (numerical average of the log reduction values). Note that an appropriate neutralizer was first determined for each formulation tested in accordance with ASTM testing method E1173-93 section 6.7. For most polymer systems the following neutralizing sampling solution was used: 0.4 g potassium dihydrogen phosphate, 10.1 g sodium hydrogen phosphate, 1.0 g TRITON X100 surfactant available from Union Carbide Corp., Houston Tex., 4.5 g lecithin (CAS #8002-43-5, available from Fisher Scientific, Fairlawn, N.J. as Cat No. 03376-250), 45.0 g TWEEN 80 (ICI), 1.0 g sodium thiosulfate, and deionized water to bring the total volume to 1 liter. The sampling solution was prepared by adding all components together and heating with stirring to approximately 60° C. until dissolved. It was then placed in containers and steam sterilized.

Certain of the quaternary polymers have been shown to have antimicrobial activity and require appropriate neutralizers as described herein. Polyanionic polymers such as polysulfonic acid polymers capable of precipitating out the quaternary polymers work well. The preferred polysulfonic acid polymers are available as AQ polyesters from Eastman Chemical Company, Kingsport, Tenn., and particularly preferred is AQ 55S, which is reported to be a linear amorphous polyester based on sodium sulfoisophthalic acid. EASTMAN AQ 55S polymer is further described as a relatively high molecular weight having a dry Tg of about 55° C. This was dispersed in water at 30% by weight in water prior to addition to the neturalization media. When necessary this was added to the sampling solution as 70 g of the 30% wt/wt solution of AQ55S in water prior to adjust the final volume to 1 liter with water.

Substantivity Test

Selected compositions were applied to the forearms of healthy volunteers. The composition was applied as a uniform wet coating in an amount of approximately 4 milligrams per square centimeter ($mg/cm^2$) and allowed to thoroughly dry (typically a minimum of 5 minutes) over an area of approximately 5×5 cm. The dried composition was exposed to running tap water at a temperature of 23° C.-24° C. and a flow rate of about 2.5 liters/minute (L/min). The water was allowed to hit the arm immediately above the test site and run down over the site. The arm was held at an angle of approximately 45 degrees and the water was allowed to drop from approximately 15 cm before it hits the arm. The time for complete loss of color was recorded. BETADINE Surgical Solution (10% povidone-iondine, "paint") was often used as a control and this typically lasts for less than 5 seconds. Compositions that are not colored may be tested by addition of a suitable colorant. The colorant should not adversely effect the substantivity and thus pigments are often employed.

Certain samples were evaluated qualitatively by applying samples in the same manner and checking for resistance to wash off, however, the time was not recorded. For these samples "very good" refers to compositions that resist wash off very well and are believed to have a substantivity value in excess of 60 seconds, "good" refers to compositions that have a substantivity value of greater than 30 seconds, and "low" refers to compositions that have a substantivity value of 15-30 seconds.

Tack Test

The tack of dried compositions was evaluated after applying to the forearms of healthy volunteers and allowing the compositions to dry. A composition was applied as a uniform wet coating in an amount of approximately 4 $mg/cm^2$ and allowed to thoroughly dry (typically a minimum of 5 minutes). The tack was evaluated by pressing a clean finger or thumb (washed and dried thoroughly) onto the composition with moderate pressure for 3-5 seconds and releasing. The tack was rated subjectively as no tack (equivalent to BETADINE Surgical Solution, i.e., 10% povidone-iondine, "paint"), very low tack (very slight sticking to the test finger, little and no visible skin deformation of the coated skin upon removal of the test finger, KLEENEX tissue can be pressed on and falls off under its own weight), low tack (slight sticking to the test finger with some upward deformation of the coated skin indicating adhesion, KLEENEX tissue can be pressed on and removed with slight or no fibers), moderate tack (sticks to the test finger with visible deformation of the coated skin upon removal, KLEENEX tissue will tear upon removal), or high tack (sticks so much that the coated skin visibly pulls up significantly as the test finger is slowly removed).

Incise Drape Adhesion Test

The adhesion of adhesive products over the compositions of the present invention was evaluated by both a qualitative use test and a quantitative peel test.

Qualitative Test: In the qualitative test, a sample was applied to the forearm as described above for the Substantivity test to one side of a forearm. On the lateral side was painted BETADINE Surgical Scrub ("scrub", 7.5% povidone-iodine) and BETADINE Surgical Solution ("paint", 10% povidone-iodine) per the manufacturer's instructions. Both were allowed to dry for at least 5 minutes. A sample of 3M IOBAN 2 Antimicrobial Incise Drape (3M Company, St. Paul, Minn.) was applied over the dried test sites and the drape worn for about 2 hours. After the wear period any lift of the incise drape was noted. The drape was removed by peeling and the adhesive was qualitatively evaluated based on the force needed to remove and the paint felt upon removal as low (less than BETADINE scrub and paint solutions), moderate (equivalent to BETADINE scrub and paint solutions), or good (better than BETADINE scrub and paint solutions).

Quantitative Test: Sixteen (16) volunteers had the test compositions applied to their backs by simply painting the site with gauze saturated with the test composition using moderate pressure three times in a continuous circular motion. The prep was allowed to dry for 5 minutes after which ½ inch (1.27 cm) wide strips of 3M IOBAN 2 Antimicrobial Incise Drape were very gently applied over the dry composition. Within 5 minutes the samples were rolled with a 4.5-lb (2.1-kilogram (kg)), 2-inch (5.1-cm) roller to ensure uniform application pressure. The drape samples were removed 10 minutes after application using a force-measuring instrument at a peel angle of 180 degrees (unless otherwise noted) and a speed of 12 inches/min (30.5 cm/min). The average force required to remove the sample over a 3-inch (7.6-cm) length was recorded. The reported value is the average of the values from all 16 subjects.

Brookfield Viscosity Test

The viscosity was measured using a Brookfield RVT ROTOVISCO viscometer commercially available from Engineering Labs Inc. (Middleboro, Mass.) with a small sample adapter (ULA adapter) LVDVI+. Measurements were taken at 23° C.-25° C. using spindle size 00 at a speed of 30 revolutions per minute (rpm).

Rabbit Eye Irritation Test

Compositions were evaluated for their potential for eye irritation compared to commercially available antiseptics: BETADINE Surgical Scrub (7.5% povidone-iodine) and BETADINE Sterile Ophthalmic Prep Solution (5% povidone-iodine). The test involved instilling into the eyes of adult New Zealand White albino rabbits weighing 2.0-3.5 Kg of either sex. Proper husbandry of the animals prior to testing is ensured including clean housing, high fiber rabbit diets (No. 5326 Purina Mills, Inc.), proper clean watering, proper environmental control (16° C.-22° C., 30%-70% relative humidity, and a 12 hour light/12 hour dark cycle). All animals were acclimated for at least 5 days and were given various cage-enrichment devices. Eyes were examined using sodium fluorscein dye on the day before the test material administration to ensure no sign of corneal injury or eye abnormality was present. Each test material was administered to three rabbits with 0.1 mL of undiluted test material/eye for two consecutive days. The eyelids were gently held together for 1 second before releasing to prevent loss of the material. The eyes of the rabbits remained unflushed for approximately 24 hours following instillation of the test material. The right eye of each animal was treated while the left eye remained untreated as a control. The eyes were examined for ocular irritation at 1, 4, 24, 48, and 72 hours after their respective treatment. Additional observations were made at 96 and 120 hours if irritation was present at 72 hours. Sodium Fluoroscein was used to aide in revealing possible corneal injury for each animal beginning with the 24-hour examination and each continuing examination until a negative response was attained. Irritation was scored using the Ocular Draize Technique (J. H. Draize: "Dermal Toxicity", *Appraisal of the Safety of Chemicals in Foods, Drugs and Cosmetics*, Association of Food and Drug Officials of the U.S., 1959, pages 46-59) with some modification. The maximum total score for these examples was the sum of scores obtained only from the conjunctivae. Total maximum score possible is 60 (20 per eye times three eyes). Notes were made with respect to the Cornea opacity, but this was not included in the scoring.

Starting Materials

Preparation Polymer A

The amounts of each chemical compound given in Table 1a were weighed into a quart-size bottle (1.06 liters) and mixed together into a homogeneous solution.

TABLE 1a

Materials used in Polymer A Preparation

| Amount (grams) | Description |
| --- | --- |
| 150.0 | 2-EHA |
| 50.0 | DMAEAMC |
| 10.0 | AM-90G |
| 0.5 | VAZO 67 |
| 190.0 | EtOH (N-190) |

The mixture in the bottle was purged with nitrogen to remove oxygen and sealed with a TEFLON fluoropolymer resin (E.I. du Pont de Nemours and Company) lined metal cap. The bottle was placed in an apparatus for rotating closed containers in a thermostatically controlled water bath at 60° C. for 24 hours. The inherent viscosity (IV) of the polymer was determined (see Test Protocol for inherent viscosity) to be 0.11 in THF. The conversion of monomer to polymer was 99.6%.

Deionized (DI) water (450 grams (g)) was added to the bottle to disperse the polymer to 23.5% solids. The dispersion was neutralized to pH=6-7 by addition of 10% NaOH solution. Next the dispersion was scavenged to reduce residual monomer levels with TBHP/SFS ratios of 700/600, 700/600, 700/500 parts per million (ppm) three times at 60° C. The scavenging reaction was performed by: 1) adding the first charge of TBHP (2.8 g of a 5% ethanol solution) and stirring for 10 minutes; 2) adding the first charge of SFS (2.4 g of a 5% aqueous solution) and stirring for another 30 minutes; 3) repeating 1) and 2) two additional times. The resulting dispersion was neutralized to pH=7-8 by addition of 10% NaOH solution, followed by stripping of ethanol under reduced pressure at 60° C. to 70° C. in a water bath. About 150 g of DI water was added during the stripping process to make up of the distilled ethanol. The final properties for the polymer dispersion were: solids, 26.8%, Mw/Mn=58.2/16.5K; Inherent Viscosity, 0.13 in THF; residual monomers, all monomers were below 10 ppm.

Preparation of Polymer B

The amounts of each chemical compound given in Table 1b were weighed into a quart-size bottle (1.06 liter) and mixed together into a homogeneous solution.

TABLE 1b

Materials used in Polymer B Preparation

| Amount (grams) | Description |
|---|---|
| 7.5 | LMA |
| 15.0 | BA, ICI |
| 75.0 | DMAEAMC |
| (80% in water) | |
| 67.5 | MMA |
| 0.375 | VAZO 67 |
| 207.0 | EtOH, anhydrous |
| 3.0 | DI water |

The mixture was degassed, sealed and polymerized as described in Preparation for Polymer A. The conversion of monomer to polymer was greater than 99.5%. DI water (375 g) was added to the bottle to disperse the polymer to 20% solids. The dispersion was scavenged to reduce residual monomer levels with TBHP/SFS ratios of 1000/1000, 800/700, 800/700 ppm three times at 60° C. as described in Preparation of Polymer A. The scavenged dispersion was distilled to remove ethanol at atmospheric pressure. D-C Additive 62 (at 0.30% based on solids) was added to control the foaming during the distillation process. The final sample was thick and clear. The analytical results for the polymer dispersion were: solids, 20.5%; Brookfield Viscosity, 6000 cps; pH=3.9; residual monomers, none except for 3 ppm DMAEAMC.

Preparation of Polymer C

The amounts of each chemical compound given in Table 1c were weighed into a quart-size bottle (1.06 liter) and mixed together into a homogeneous solution.

TABLE 1c

Materials used in Polymer C Preparation

| Amount (grams) | Description |
|---|---|
| 7.5 | LMA |
| 37.5 | IBMA |
| 52.5 | DMAEMA |
| 52.5 | MMA |
| 0.75 | VAZO 67 |
| 350 | EtOH, anhydrous |

The mixture was degassed, sealed, and polymerized as described in Preparation for Polymer A except at 75° C. for 16 hours. The conversion of monomer to polymer was 97.4% and the inherent viscosity was 0.33 in THF.

Next 25 g of a 50% aqueous solution of $H_2O_2$ ($H_2O_2$/amine molar ratio=1.1) was added to the polymer to oxidize the tertiary amine to amine oxide at 60° C. for 20 hours.

The oxidized polymer was mixed with DI water in equal parts to form a clear aqueous dispersion. The dispersion was scavenged with TBHP/SFS ratios of 1000/1000, 1000/1000, 1000/1000 ppm at 60° C. three times as was described in Preparation of Polymer A. Next ethanol was stripped off under reduced pressure with about 0.05% D-C Additive 62 defoamer. The stripped ethanol was replaced with 155 g of DI water. The final dispersion had the following properties: solids, 17.1%; Brookfield viscosity, 19600 cps; pH=7.7; residual monomers, LMA/IBMA/DMAEMA/MMA=570/770/none detected/75 ppm based on polymer solids.

General Composition Preparation for Examples

The compositions of the present invention were prepared in the following manner. For compositions incorporating povidone-iodine (PVP-I) the PVP-I was first dissolved in DI water at 30% solution by weight. In general, the addition order is not important, however, it is preferred to follow the general order listed below:

a. Weigh into the sample jar all hydrolytically stable nonionic surfactants especially those that may be solids and may require heating to dissolve, e.g., BRIJ 700.

b. Add the water, mix, and heat if necessary (e.g., to about 60° C.) to dissolve any surfactants/polymers which may take 1-2 hours.

c. Add in buffer components one at a time with complete mixing in between additions.

d. Adjust pH by addition of 5N sodium hydroxide to about 2.5-6.0, preferably 3.5-4.0. The amount of sodium hydroxide is taken into account in the amount of water.

e. Optionally, add in any surfactants that may not be as hydrolytically stable, e.g., surfactants comprising ester linkages.

f. Optionally add in any anionic surfactants.

g. Add antimicrobial or other active agent, e.g. PVP-I as a 30% solution concentrate in water.

h. Add the film-forming polymer solution and mix.

i. Make any final pH adjustments that may be necessary.

Examples 1 and 2 and Comparative Examples A and B

The compositions shown in Table 2a were prepared using the general procedure described above. The quaternary amine functional polyacrylate terpolymer was prepared with the general procedure for Preparation of Polymer A except the monomer levels were altered to 75/20/5 of 2-EHA/DMAEAMC/AM-90G.

TABLE 2a

Compositions of Examples 1 and 2

| Component | CAS No. | Example 1 (amount in weight percent) | Example 2 (amount in weight percent) |
|---|---|---|---|
| Terpolymer of 75/20/5 of 2-EHA/DMAEAMC/AM-90G | | 5.0 | 5.0 |
| PVP-I | | 7.5 | 7.5 |
| POLYSTEP B22 | 32612-48-9 | 5.0 | 0.0 |
| EtOH | 64-17-5 | 1.0 | 5.0 |
| Lactic Acid | 79-33-4 | 6.0 | 10.0 |
| Citric Acid | 5949-29-1 | 0.0 | 3.0 |
| MMB glycol | 56539-66-3 | 0.0 | 10.0 |
| NIKKOL TL-10 | 9005-64-5 | 0.0 | 5.0 |
| Water | | 75.5 | 54.5 |

The pH of Examples 1 and 2 was 4. The compositions were evaluated for their potential for irritation compared to two commercially available antiseptics: BETADINE Surgical Scrub (7.5% povidone-iodine) (Comparative Example A) and BETADINE Sterile Ophthalmic Prep Solution (5% povidone-iodine) (Comparative Example B). The test protocol for rabbit eye irritation was described above. The results are shown in Table 2b. The numeric scores are for redness and chemosis only as a simple addition of total scores for all animals.

TABLE 2b

The Results of the Rabbit Eye Irritation Test for Examples 1 and 2 and Comparative Examples A and B

| Example No. | 1 hour | 24 hours | 48 hours | 72 hours | 96 hours | 7 days |
|---|---|---|---|---|---|---|
| Comparative Example B | 9(B[1][3]) | 7(B1) | 0 | — | — | — |
| Comparative Example A | 10 | 9 | 8 | 3 | 2 | 0 |
| Example 1 | 7(C[2]1) | 3 | 2 | 0 | — | — |
| Example 2 | 10(B1) | 11(B1) | 7 | 5 | 0 | — |

[1]B means blanching of the conjunctiva tissue
[2]C means corneal opacity
[3]Numerical value after the alpha code indicates the number of animals involved

Examples 3-11

The compositions shown in Table 3a were prepared using the general procedure described above. The quarternary amine functional polyacrylate polymers were prepared with the general procedure for Preparation of Polymer A except the monomer levels were altered to 75/20/5 of 2-EHA/DMAE-AMC/AM-90G.

The compositions were evaluated for their potential for irritation compared to two commercially available antiseptics as described for Examples 1 and 2. The results are shown in Table 3b. The numeric scores are for redness and chemosis only as a simple addition of total scores for all animals.

TABLE 3a

Compositions and pH of Examples 3-11

| Component | 3 | 4 | 5 | 6 | 7 | 8 | 9 | 10 | 11 |
|---|---|---|---|---|---|---|---|---|---|
| Terpolymer of 75/20/5 of 2-EHA/DMAEAMC/AM-90G | 5.0 | 5.0 | 5.0 | 5.0 | 5.0 | 5.0 | 5.0 | 5.0 | 5.0 |
| PVP-I | 7.5 | 7.5 | 7.5 | 7.5 | 7.5 | 7.5 | 7.5 | 0.0 | 0.0 |
| POLYSTEP B22 | 0.0 | 0.0 | 0.0 | 0.0 | 5.0 | 0.0 | 0.0 | 0.0 | 0.0 |
| EtOH | 5.0 | 5.0 | 5.0 | 5.0 | 0.0 | 5.0 | 5.0 | 5.0 | 5.0 |
| Lactic Acid | 5.0 | 5.0 | 5.0 | 3.0 | 5.0 | 3.0 | 0.0 | 5.0 | 3.0 |
| Mandelic Acid | 0.0 | 0.0 | 0.0 | 0.0 | 0.8 | 0.0 | 0.0 | 0.0 | 0.0 |
| Citric Acid | 6.0 | 8.0 | 8.0 | 3.0 | 8.0 | 5.0 | 8.0 | 6.0 | 3.0 |
| DL Malic Acid | 0.0 | 0.0 | 0.0 | 5.0 | 0.0 | 5.0 | 5.0 | 0.0 | 0.0 |
| Propylene glycol | 0.0 | 5.0 | 5.0 | 0.0 | 5.0 | 0.0 | 0.0 | 5.0 | 5.0 |
| NIKKOL TL 10 | 5.0 | 5.0 | 5.0 | 5.0 | 5.0 | 5.0 | 5.0 | 0.0 | 0.0 |
| Water | 66.5 | 59.5 | 59.5 | 66.5 | 58.7 | 64.5 | 64.5 | 74.0 | 79.0 |
| Total Concentration of Organic Acid | 11.0 | 13.0 | 13.0 | 11.0 | 13.8 | 13.0 | 13.0 | 11.0 | 11.0 |
| pH | 3.5 | 4.0 | 3.2 | 3.5 | 3.5 | 4.0 | 3.5 | 3.5-4.0 | 3.5-4.0 |

TABLE 3b

Results of the Rabbit Eye Irritation Test for Examples 3-9

| Example No. | Numeric Ranking[4] | 1 hour | 4 hours | 24 hours | 48 hours | 72 hours | 96 hours | 7 days |
|---|---|---|---|---|---|---|---|---|
| Comparative Example A | 9 | 11(B[1]2[3]) | 15(B2, C1) | 14(B3, C2) | 10(C1) | 4 | 0 | — |
| Comparative Example B | 3 | 10(B1) | 11(B1) | 4 | 0 | — | — | — |
| 3 | 7 | 12(B1) | 11 | 8 | 6 | 0 | — | — |
| 4 | 6 | 11(B1) | 9(B1) | 10 | 4 | 0 | — | — |
| 5 | 5 | 8(C[2]1) | 8 | 7 | 4 | 0 | — | — |
| 6 | 4 | 11(B1) | 10 | 5 | 0 | — | — | — |
| 7 | 8 | 11 | 11(B3) | 11(B1) | 7(B1) | 0 | — | — |
| 8 | 2 | 10(B1) | 9(B1) | 5 | 0 | — | — | — |
| 9 | 1 | 9 | 7 | 0 | — | — | — | — |

[1]B means blanching of the conjunctiva tissue
[2]C means corneal opacity
[3]Numerical value after the alpha code indicates the number of animals involved
[4]Numerical ranking was calculated by adding total scores from all test times and taking into account blanching and corneal opacity values The results indicate that despite the high levels of organic acid buffers all of the compositions were more gentle than BETADINE Surgical Scrub (Comparative Example A), which has been widely used for many years on skin and mucosal tissue (although it is not indicated for use on mucosal tissue). In addition, Examples 8 and 9 were shown to be more gentle than BETADINE Sterile Ophthalmic Prep Solution (Comparative Example B). All eyes treated with the compositions of the present invention had no irritation perceptible after 72 hours. Surprisingly, Examples 6 and 8 had no irritation perceptible after only 48 hours. Example 9 had no irritation perceptible after only 24 hours.

Examples 12-17

The compositions shown in Table 4a were prepared using the general procedure described above. The quarternary amine functional polyacrylate polymers were prepared with the general procedure for Preparation of Polymer A (2-EHA) or Preparation of Polymer C (LMA) except the monomer levels were altered to 15/35/50 of 2-EHA/DMAEAMC/MMA and 5/10/40/45 of LMA/BA/DMAEMAC/MMA respectively. The pH for all these compositions was 3.5-4.

TABLE 4a

Compositions of Examples 12-17

| Component | Example Number (Amounts in weight percents) | | | | | |
|---|---|---|---|---|---|---|
| | 12 | 13 | 14 | 15 | 16 | 17 |
| 2-EHA/DMAEAMC/MMA 15/35/50 | 0.00 | 0.00 | 0.00 | 3.50 | 0.00 | 0.00 |
| LMA/BA/DMAEMAC/MMA 5/10/40/45 | 3.50 | 0.00 | 3.50 | 0.00 | 0.00 | 3.50 |
| DIAFORMER Z-731 | 0.00 | 5.00 | 2.50 | 2.50 | 5.00 | 0.00 |
| PVP-I | 7.50 | 7.50 | 7.50 | 7.50 | 7.50 | 7.50 |
| Lactic Acid | 5.00 | 5.00 | 5.00 | 5.00 | 5.00 | 5.00 |
| DL Malic Acid | 2.00 | 2.00 | 2.00 | 2.00 | 2.00 | 2.00 |
| NIKKOL TL 10 | 1.50 | 1.25 | 1.50 | 1.50 | 1.50 | 1.00 |
| BRIJ 700 | 1.50 | 1.00 | 1.00 | 1.00 | 0.85 | 1.50 |
| Water | 79.00 | 78.25 | 77.00 | 77.00 | 78.15 | 79.50 |
| Total Concentration of Organic Acid | 7 | 7 | 7 | 7 | 7 | 7 |

The compositions were evaluated for their potential for irritation compared to two commercially available antiseptics as described for Examples 1 and 2. The results are shown in Table 4b. The numeric scores are for redness and chemosis only as a simple addition of total scores for all animals.

TABLE 4b

Results of Rabbit Eye Irritation Test for Examples 12-17

| Example No. | Time | | | | | | |
|---|---|---|---|---|---|---|---|
| | 1 hour | 4 hours | 24 hours | 48 hours | 72 hours | 96 hours | 7 days |
| Comparative Example A | 12 | 16 (B[1]3[2]) | 14 (B2) | 12 (B2) | 10 (B2) | 7 | 4 |
| Comparative Example B | 10 | 12 | 7 | 1 | 1 | 0 | — |
| 12 | 9 | 9 | 4 | 1 | 1 | 0 | — |
| 13 | 9 | 9 | 3 | 1 | 0 | — | — |
| 14 | 10 | 10 | 5 | 2 | 2 | 2 | 0 |
| 15 | 9 | 9 | 6 | 2 | 2 | 2 | 0 |
| 16 | 9 | 8 | 4 | 0 | — | — | — |
| 17 | 8 | 8 | 6 | 1 | 1 | 0 | — |

[1]B means blanching of the conjunctiva tissue
[2]Numerical value after the alpha code indicates the number The results indicate that despite the high levels of organic acid buffer (7% by weight) all compositions had approximately the same potential for irritation as BETADINE Sterile Ophthalmic Prep Solution (Comparative Example B) and were far less irritating than BETADINE Surgical Scrub (Comparative Example A). The type of polymer or blend of polymers did not significantly alter the irritation potential. The Examples with the lowest level of surfactant and the amine oxide functional polymer, 13 and 16, showed the least irritation.

Examples 18-21

The compositions shown in Table 5a were prepared using the general procedure described above. The quarternary amine functional polyacrylate polymers were prepared with the general procedure for Preparation of Polymer A (2-EHA) and the same polymer that was used in Example 1 was used in the compositions for Examples 18-21. The pH for each of these compositions was 3-4.

TABLE 5a

Compositions of Examples 18-21

| Component | Example Number (Amounts in weight percents) | | | |
|---|---|---|---|---|
| | 18 | 19 | 20 | 21 |
| 2-EHA/DMAEAMC/AM-90G 75/20/5 | 5.00 | 5.00 | 5.00 | 5.00 |
| PVP-I | 7.50 | 7.50 | 7.50 | 7.50 |
| POLYSTEP B22 | 0.00 | 0.00 | 3.00 | 0.00 |
| Ethanol | 5.00 | 5.00 | 5.00 | 5.00 |
| Lactic Acid | 3.00 | 5.00 | 0.80 | 0.00 |
| Mandelic acid | 0.00 | 0.00 | 0.80 | 0.00 |
| Citric Acid | 6.00 | 6.00 | 8.00 | 8.00 |
| DL Malic Acid | 0.00 | 0.00 | 0.00 | 5.00 |
| Propylene glycol | 5.00 | 0.00 | 0.00 | 0.00 |
| NIKKOL TL10 | 5.00 | 5.00 | 5.00 | 5.00 |
| Water | 63.5 | 66.5 | 64.9 | 64.5 |

The compositions were evaluated for antimicrobial activity on skin as described in the test method given above in a single panel of subjects each tested on all 8 of the subjects. Total aerobic bacteria log reduction was determined. The concentration of alpha-hydroxy acids (AHA) was varied over a significant range. The molar concentration is shown in Table 5b, as is the antimicrobial activity (log reduction, last row).

TABLE 5b

Molar Concentration of Alpha-hydroxy acids for
Examples 18-21 and Antimicrobial Activity

| Component | Example Number | | | |
|---|---|---|---|---|
| (Moles) | 18 | 19 | 20 | 21 |
| AHA | 0.65 | 0.87 | 0.51 | 0.79 |
| LA + MLA (M) | 0.33 | 0.56 | 0.09 | 0.37 |
| CA (M) | 0.31 | 0.31 | 0.42 | 0.42 |
| LA (M) | 0.33 | 0.56 | 0.09 | 0.00 |
| MLA (M) | 0.00 | 0.00 | 0.00 | 0.37 |
| Antimicrobial Activity | 1.8 | 2.4 | 1.4 | 1.9 |

Figure 2:
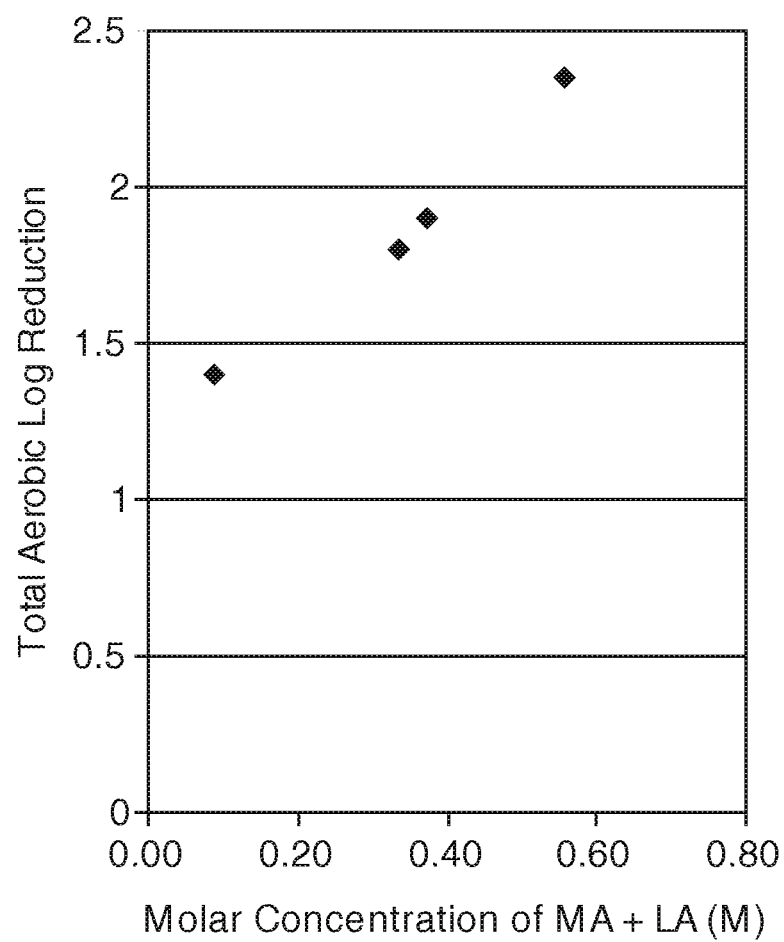
FIG. 2. Antimicrobial activity results plotted as a function of only the concentration of lactic acid (LA)+malic acid (MA).

The antimicrobial activity results were plotted as a function of total molar concentration of alpha-hydroxy acid (FIG. 1) and as a function of only the concentration of Lactic acid (LA)+malic acid (MA) (FIG. 2). The results indicated that the log reduction seen on skin appeared to be directly related to the level of AHA in the composition at high levels of AHA.

Examples 22-43

Example 22-43 illustrate the use of anionic detergent type surfactants in combination with the amine group-containing film-forming polymers. The anionic detergent type surfactants used in these examples are described in Table 6a.

TABLE 6a

Anionic detergent type surfactants used in Examples 22-43

| Trade Mark Name | Chemical Description | CAS Number | Source | Address |
|---|---|---|---|---|
| ALPHASTEP PC-48 | Sodium methyl-2-sulfoC12-16 ester and disodium2-sulfo C12-16 fatty acid | 149458-07-1 | Stepan | Northfield, IL |
| MACKAM 50-SB | Cocoamidopropylhydroxy sultaine | 68139-30-0 | McIntyre Group Ltd | University Park, IL |
| AMMONYX LMDO | C12-14 amidopropyldimethylamine oxide | Confidential | Stepan | Northfield, IL |
| AMMONYX LO | lauryldimethylamine oxide | 1643-20-5 | Stepan | Northfield, IL |
| POLYSTEP A16 | sodium dodecylbenzenesulfonate | 68608-89-9 | Stepan | Northfield, IL |
| POLYSTEP B11 | Ammonium lauryl ether sulphate (4 moles ethyleneoxide) | | Stepan | Northfield, IL |
| WITCONATE 60T | C10-C13 alkylbenzenesulfonic acid, Triethanolamine salt | 68411-31-4 | Crompton Corp | Greenwich CT |
| STEPANOL WAT | TEA laurylsulfate | 139-96-8 | Stepan | Northfield, IL |
| STEPANMILD SL3 | disodium laureth (3 mole) sulfosuccinate | 39354-45-5 | Stepan | Northfield, IL |
| STEOL CS330 | Ammonium laureth sulfate | | Stepan | Northfield, IL |
| HOSTAPHAT KL 340D | Mono, di and tri-lauryltetraglcyolether-o-phosphoric acid esters | mixture | Clariant | Charlotte, NC |
| ISOFOL 12 SULFATE | 2butyloctylsulfate, sodium salt | 94200-74-5 | Condea Vista | Houston TX |
| ISOFOL 16 SULFATE | 2hexyldecyl sulfate sodium salt | 25542-86-3 | Condea Vista | Houston TX |
| MASKAM JS | Sodium caprylamphohydroxysulfonate | 68610-39-9 | McIntyre | University Park, IL |
| CRODAFOS SG | PPG-5-Ceteth 10 phosphate | 73361-29-2 | Croda, Inc | Parsippany, NJ |
| RHODAPEX CO-436 | Ammonium nonylphenol ether sulfate, branched | 68649-55-8 | Rhodia | Dayton, NJ |
| HOSTAPON CT | sodium methylcocoyltaurate | 61791-42-2 | Clariant | Charlotte, NC |
| HOSTAPUR SAS-60 | sodium C14-17 sec alkylsulfonate | 85711-69-9 | Clariant | Charlotte, NC |
| HOSTAPON SCI 85 | Sodium cocoylisethionate (85% actives) | 61789-32-0 | Clariant | Charlotte, NC |

A base composition was prepared using LMA/MMA/trimethylaminoethylmethacrylate chloride salt/BA produced by preparation of Polymer B described above. The components and the amounts and weight percent of each are shown in Table 6b.

TABLE 6b

Base composition used in Examples 22-43

| Component | Amount (grams) | Amount (weight percent solids) |
|---|---|---|
| LMA/MMA/Trimethylaminoethyl methacrylate chloride salt/BA (20.5% solids) | 4.27 | 3.5 |
| PVP-I (30% solids) | 6.25 | 7.5 |
| 20% BRIJ 700 | 1.88 | 1.5 |
| Lactic Acid (88% solution) | 1.42 | 5.0 |
| Malic Acid | 0.50 | 2.0 |
| 5N NaOH | 1.90 | 7.6 |
| NIKKOL TL10 | 0.38 | 1.5 |
| Water | 8.41 | |
| Total | 25.00 | |

Various surfactants were added to aliquots of the composition of Table 6b. The compositions were mixed well for several hours. The stability of the compositions was evaluated by two methods. In the first method the vial was held up to a bright over-head fluorescent light to evaluate clarity and color. In the second method the vial full of composition was evaluated using a very bright small illuminator (Model 78103, Vaginal Illuminator System F/58001, Welch-Allyn, Skaneateles Falls, N.Y.) The illuminator light source was placed directly on the bottom of the vial and the sample evaluated paying particular attention to the light path. Completely transparent samples, such as a solution of 10% povidone-iodine USP, appeared transparent with a light path that went almost straight through the vial with very little light diffraction. Samples that appeared cloudy by the fluorescent light evaluation method when tested with the illuminator often showed a light path that was conical and more diffuse. The stability was evaluated initially and after 4 days at 23° C.

and 60° C. The compositions and results of the stability test are described in Tables 6c, 6d, 6e, 6f, 6g, 6h. The percentages are percent solids. Each of the compositions had a pH of 3.5-4. The terms used to describe stability are: transparent means that the composition was a completely stable transparent solution when evaluated by both the fluorescent light and the illuminator; cloudy means that the composition appeared cloudy under the fluorescent light and illuminator and showed a diffuse light path with the illuminator. These samples were physically stable with no separation unless otherwise noted. Since they were not transparent a possible interaction may have occurred; precipitate means that a phase separation occurred usually accompanied by settling, which was usually visible under the fluorescent light and definitely visible under the illuminator; mocha means a more opaque appearance similar to mocha chocolate drinks under the fluorescent light. With the illuminator these mocha samples may or may not have appeared cloudy; and hazy means slightly cloudy under the fluorescent light but when evaluated with the illuminator the composition appeared transparent, but still was stable with no phase separation.

TABLE 6c

Compositions and Results of Stability Tests for Examples 22-25

| | Example 22 Amount | | Example 23 Amount | | Example 24 Amount | | Example 25 Amount | |
|---|---|---|---|---|---|---|---|---|
| Component | grams | % solid component in solution | grams | % solid component in solution | grams | % solid component in solution | grams | % solid component in solution |
| Base Composition (Table 6b) | 24.56 | | 24.13 | | 24.58 | | 24.75 | |
| WITCONATE 60T (57%) | 0.44 | 1.0 | 0.00 | | 0.00 | | 0.00 | |
| HOSTAPON CT paste (28.6%) | 0.00 | | 0.87 | 1.0 | 0.00 | | 0.00 | |
| POLYSTEP B11 (59.2%) | 0.00 | | 0.00 | | 0.42 | 1.0 | 0.00 | |
| HOSTAPON SCI 85 (85%) | 0.00 | | 0.00 | | 0.00 | | 0.30 | 1.0 |
| LMA/MMA/trimethylaminoethyl methacrylate chloride salt/BA (20.5% solids) | | 3.4 | | 3.4 | | 3.4 | | 3.5 |
| PVP-I (30% solids) | | 7.4 | | 7.2 | | 7.4 | | 7.4 |
| Total | 25.00 | | 25.00 | | 25.00 | | 25.00 | |
| Stability at 23° C. after 4 days | cloudy/brown | | transparent/dark brown | | precipitate | | precipitate | |
| Stability at 60° C. after 4 days | cloudy/brown | | transparent | | precipitate | | precipitate | |

TABLE 6d

Compositions and Results of Stability Tests for Examples 26-29

| | Example 26 Amount | | Example 27 Amount | | Example 28 Amount | | Example 29 Amount | |
|---|---|---|---|---|---|---|---|---|
| Component | grams | % solid component in solution | grams | % solid component in solution | grams | % solid component in solution | grams | % solid component in solution |
| Base Composition (Table 6b) | 23.89 | | 24.11 | | 24.58 | | 24.00 | |
| HOSTAPHAT KL 340-D (90%) | 0.28 | 1.0 | 0.00 | | 0.00 | | 0.00 | |
| STEOL CS-330 (28%) | 0.00 | | 0.89 | 1.0 | 0.00 | | 0.00 | |
| HOSTAPUR SAS-60 (60%) | 0.00 | | 0.00 | | 0.42 | 1.0 | 0.00 | |
| STEPANMILD SL3 (33.7%) | 0.00 | | 0.00 | | 0.00 | | 1.00 | 1.35 |
| LMA/MMA/trimethylaminoethyl methacrylate chloride salt/BA (20.5% solids) | | 3.3 | | 3.4 | | 3.4 | | 3.4 |
| PVP-I (30% solids) | | 7.2 | | 7.2 | | 7.4 | | 7.2 |
| Total | 25.00 | | 25.00 | | 25.00 | | 25.00 | |
| Stability at 23° C. after 4 days | transparent/dark brown | | hazy/mocha | | cloudy/brown | | precipitate/mocha | |
| Stability at 60° C. after 4 days | hazy/dark brown | | hazy/mocha | | cloudy/precipitate | | precipitate/mocha | |

TABLE 6e

Compositions and Results of Stability Tests for Examples 30-33

| Component | Example 30 Amount grams | Example 30 % solid component in solution | Example 31 Amount Grams | Example 31 % solid component in solution | Example 32 Amount grams | Example 32 % solid component in solution | Example 33 Amount grams | Example 33 % solid component in solution |
|---|---|---|---|---|---|---|---|---|
| Base Composition (Table 6b) | 23.52 | | 24.50 | | 24.75 | | 24.57 | |
| ALPHASTEP PC 48 (38.8%) | 0.64 | 1.0 | 0.00 | | 0.00 | | 0.00 | |
| MACKAM 50-SB (50%) | 0.00 | | 0.50 | 1.0 | 0.00 | | 0.00 | |
| CRODAPHOS SG | 0.00 | | 0.00 | | 0.25 | 1.0 | 0.00 | |
| RHODAPLEX CO 436 (58%) | 0.00 | | 0.00 | | 0.00 | | 0.43 | 1.0 |
| AMMONYX LMDO (30%) | 0.83 | 1.0 | 0.00 | | 0.00 | | 0.00 | |
| LMA/MMA/trimethylaminoethyl methacrylate chloride salt/BA (20.5% solids) | | 3.3 | | 3.4 | | 3.5 | | 3.4 |
| PVP-I (30% solids) | | 7.1 | | 7.4 | | 7.4 | | 7.4 |
| Total | 25.00 | | 25.00 | | 25.00 | | 25.00 | |
| Stability at 23° C. after 4 days | Precipitate | | transparent/dark | | cloudy | | precipitate | |
| Stability at 60° C. after 4 days | Precipitate | | transparent/dark | | light precipitate | | precipitate | |

TABLE 6f

Compositions and Results of Stability Tests for Examples 34-37

| Component | Example 34 Amount grams | Example 34 % solid component in solution | Example 35 Amount grams | Example 35 % solid component in solution | Example 36 Amount grams | Example 36 % solid component in solution | Example 37 Amount grams | Example 37 % solid component in solution |
|---|---|---|---|---|---|---|---|---|
| Base Composition (Table 6b) | 24.17 | | 24.17 | | 23.73 | | 23.17 | |
| AMMONYX LO (30%) | 0.83 | 1.0 | 0.00 | | 0.00 | | 0.00 | |
| AMMONYX LMDO (30%) | 0.00 | | 0.83 | 1.0 | 0.00 | | 0.83 | 1.0 |
| WITCONATE 60T (57%) | 0.00 | | 0.00 | | 0.44 | 1.0 | 0.00 | |
| STEPANMILD SL3 (33.7%) | 0.00 | | 0.00 | | 0.00 | | 1.00 | 1.35 |
| LMA/MMA/trimethylaminoethyl methacrylate chloride salt/BA (20.5% solids) | | 3.4 | | 3.4 | | 3.3 | | 3.2 |
| PVP-I (30% solids) | | 7.3 | | 7.3 | | 7.1 | | 7.0 |
| Total | 25.00 | | 25.00 | | 25.00 | | 25.00 | |
| Stability at 23° C. after 4 days | transparent/dark | | transparent/dark | | cloudy | | transparent/dark | |
| Stability at 60° C. after 4 days | transparent/dark | | transparent/dark | | precipitate | | transparent/dark | |

TABLE 6g

Compositions and Results of Stability Tests for Examples 38-41

| Component | Example 38 Amount Grams | Example 38 % solid component in solution | Example 39 Amount grams | Example 39 % solid component in solution | Example 40 Amount grams | Example 40 % solid component in solution | Example 41 Amount grams | Example 41 % solid component in solution |
|---|---|---|---|---|---|---|---|---|
| Base Composition (Table 6b) | 23.74 | | 23.87 | | 23.92 | | 23.27 | |
| POLYSTEP B11 (59.2%) | 0.42 | 1.0 | 0.00 | | 0.00 | | 0.00 | |
| HOSTAPON SCI 85 (85%) | 0.00 | | 0.30 | 1.0 | 0.00 | | 0.00 | |
| CRODAFOS SG | 0.00 | | 0.00 | | 0.25 | 1.0 | 0.00 | |
| STEOL CS-330 (28%) | 0.00 | | 0.00 | | 0.00 | | 0.89 | 1.0 |
| AMMONYX LMDO (30%) | 0.83 | 1.0 | 0.83 | 1.0 | 0.83 | 1.0 | 0.83 | 1.0 |
| LMA/MMA/trimethylaminoethyl methacrylate chloride salt/BA (20.5% solids) | | 3.3 | | 3.3 | | 3.3 | | 3.3 |
| PVP-I (30% solids) | | 7.1 | | 7.2 | | 7.2 | | 7.0 |
| Total | 25.00 | | 25.00 | | 25.00 | | 25.00 | |
| Stability at 23° C. after 4 days | Cloudy | | cloudy | | transparent/dark | | transparent/dark | |
| Stability at 60° C. after 4 days | transparent/dark | | transparent/dark/ fine precipitate with illuminator | | transparent/dark | | transparent/dark | |

TABLE 6h

Compositions and Results of Stability Tests for Examples 42-43

| Component | Example 42 Amount grams | Example 42 % solid component in solution | Example 43 Amount grams | Example 43 % solid component in solution |
|---|---|---|---|---|
| Base Composition (Table 6b) | 23.75 | | 23.74 | |
| HOSTAPUR SAS-60 (60%) | 0.42 | 1.0 | 0.00 | |
| RHODAPLEX CO-436 (58%) | 0.00 | | 0.43 | 1.0 |
| AMMONYX LMDO (30%) | 0.83 | 1.0 | 0.83 | 1.0 |
| LMA/MMA/ trimethylamino-ethyl methacrylate chloride salt/BA (20.5% solids) | | 3.3 | | 3.3 |
| PVP-I (30% solids) | | 7.1 | | 7.1 |
| Total | 25.00 | | 25.00 | |
| Stability at 23° C. after 4 days | cloudy | | transparent/ dark | |
| Stability at 60° C. after 4 days | precipitate/ cloudy/ mocha | | transparent/ mocha | |

The results show that in general most of the anionic surfactants were not capable of forming transparent/dark solutions in combination with the quaternary amine polymer. The sultaine and amine oxide surfactants did form transparent/dark solutions in combination with the quaternary amine functional polymer. Certain surfactants such as lauramidopropyldimethylamine oxide can promote stability of certain anionic surfactants. It appears that the alkylalkoxylated anionic surfactants are more compatible in general. For example, STEOL CS330, CRODAFOS SG, STEPANMILD SL3, and RHODAPEX CO436 are all formed from alkoxylated alcohols and all formed transparent dark solutions in the presence of AMMONYX LMDO.

Examples 44-53

Examples 44-53 were prepared using an amine oxide functional polymer, DIAFORMER Z731. The DIAFORMER Z731 was received in ethanol. The water was added and the ethanol stripped out on a rotary evaporator to yield a solution, which was 17% solids. The DIAFOMER Z731 amine oxide groups can be protonated at low pH to yield a polymer which will be positively charged. A sample was titrated to determine the pKa of the polymer. This was determined by starting at high pH (e.g. 8) and titrating with HCl to low pH and then back again. Multiple pKa values were obtained. This would be expected due to the multiple arrangements of the amine oxide groups in the copolymer. The data was analyzed and it was found that at a pH of 4 close to 100% of the amine oxide groups are protonated. The amine equivalent weight also was calculated and found to be approximately 330 g polymer/ equivalent amine Despite the fact that this polymer would be highly charged it is surprising compatible with moderate levels (less than 2%) of many anionic surfactants. The level of surfactant was not increased too far to ensure the formulations had adequate substantivity on skin. The compositions, pH, stability, and substantivity for these examples are listed in Tables 7a and 7b. In Tables 7a and 7b the amounts of all components are given on a solids basis. By this it is meant that if a particular component is added as a solution in water the water is not included in the quantity of this component but rather reflected in the total amount of water in the composition.

TABLE 7a

Compositions, pH, Stability, and Substantivity for Examples 44-51

| Component | 44 weight % | 45 weight % | 46 weight % | 47 weight % | 48 weight % | 49 weight % | 50 weight % | 51 weight % |
|---|---|---|---|---|---|---|---|---|
| DIAFORMER Z-731 | 5.00 | 5.00 | 5.00 | 5.00 | 5.00 | 5.00 | 5.00 | 5.00 |
| Povidone-Iodine USP | 7.50 | 7.50 | 7.50 | 7.50 | 7.50 | 7.50 | 7.50 | 7.50 |
| Lactic Acid | 6.50 | 5.00 | 5.00 | 5.00 | 5.00 | 5.00 | 5.00 | 5.00 |
| Malic Acid | 2.50 | 2.00 | 2.00 | 2.00 | 2.00 | 2.00 | 2.00 | 2.00 |
| NIKKOL TL10 | 1.50 | 0.00 | 0.00 | 0.00 | 0.00 | 0.00 | 1.50 | 0.00 |
| BRIJ 700 | 2.00 | 1.00 | 1.00 | 1.00 | 0.00 | 0.00 | 2.00 | 1.00 |
| ALPHASTEP PC-48 | 1.00 | 0.00 | 0.00 | 0.00 | 0.00 | 0.00 | 0.00 | 0.00 |
| MACKAM 50-SB | 0.00 | 1.00 | 0.00 | 0.00 | 0.00 | 0.00 | 0.00 | 0.00 |
| CRODAPHOS SG | 0.00 | 0.00 | 0.00 | 1.00 | 0.00 | 0.00 | 0.00 | 0.00 |
| AMMONYX LMDO (30%) | 0.00 | 0.00 | 0.00 | 1.00 | 1.00 | 1.00 | 1.00 | 1.00 |
| STEPANMILD SL3 | 0.00 | 0.00 | 0.67 | 0.00 | 0.00 | 0.00 | 0.00 | 0.00 |
| POLYSTEP A16 | 0.00 | 0.00 | 0.00 | 0.00 | 0.00 | 1.00 | 0.00 | 0.00 |
| WITCONATE 60T | 0.00 | 0.00 | 0.00 | 0.00 | 0.57 | 0.00 | 0.00 | 0.00 |
| STEPANOL WAT | 0.00 | 0.00 | 0.00 | 0.00 | 0.00 | 0.00 | 1.00 | 0.00 |
| RHODAPEX CO-436 | 0.00 | 0.00 | 0.00 | 0.00 | 0.00 | 0.00 | 0.00 | 1.16 |
| Water | 74.00 | 78.50 | 78.83 | 77.5 | 78.93 | 78.5 | 75 | 77.34 |
| pH | 3.5-4 | 3.5-4 | 3.5-4 | 3.5-4 | 3.5-4 | 3.5-4 | 3.5-4 | 3.5-4 |
| Stability at 23° C. after 4 days | transparent/ dark | transparent/ dark | transparent/ dark | transparent/ dark | transparent/ dark | transparent/ dark | transparent/ dark | transparent/ dark |
| Stability at 60° C. after 4 days | transparent/ dark | transparent/ dark | transparent/ dark | transparent/ dark | transparent/ dark | transparent/ dark | transparent/ dark | transparent/ dark |
| Substantivity (sec) | >>60 | >>60 | 50-60 | 50 | 60 | >60 | >60 | 40 |

TABLE 7b

Compositions, pH, Stability, and Substantivity for Examples 52-53

|  | Example Number | |
|---|---|---|
| Component | 52 wt-% | 53 wt-% |
| DIAFORMER Z-731 | 5.00 | 5.00 |
| Povidone-Iodine USP | 7.50 | 7.50 |
| Lactic Acid | 5.00 | 5.00 |
| Malic Acid | 5.00 | 2.00 |
| NIKKOL TL10 | 1.50 | 0.00 |
| BRIJ 700 | 0.00 | 1.00 |
| CRODAPHOS SG | 1.00 | 0.00 |
| MACKAM JS | 0.00 | 1.00 |
| Water | 75.00 | 78.5 |
| pH | 3.5-4 | 3.5-4 |
| Stability at 23° C. after 4 days | transparent/dark | transparent/dark |
| Stability at 60° C. after 4 days | transparent/dark | transparent/dark |
| Substantivity (sec) | >60 | >>60 |

The data indicates that the amine oxide side-chain functional substantive polymer, DIAFORMER Z731, is surprisingly compatible with a wide variety of anionic surfactants. The presence of a co-surfactant such as an amine oxide (AMMONYX LMDO) appears to help stability as it did for the quaternary polymers as well. Despite the addition of these detergent type surfactants, which are widely used in shampoos, soaps and other cleaners to facilitate removal of dirt, oil, etc. the substantivity to skin was excellent.

Examples 54-63

Examples 54-63 illustrate the use of a quaternary ammonium side-chain functional polyacrylate polymer having an additional hydrophilic monomer (a polyethoxylated acrylate, AM-90G) and an amine equivalent weight of 1039 g polymer/equivalent quaternary amine which is a PSA at room temperature. These compositions were prepared as outlined above for Preparation Polymer A and the General Composition Preparation using the components listed in Tables 8a and 8b.

Compositions were evaluated for human skin antimicrobial activity on human volunteers as described in the test protocol using the 30-second "scrub" application technique. Compositions were also evaluated for substantivity, tack, and incise drape adhesion as outlined in the test protocols. The results are shown in Table 8a and 8b. The quantities of all components are given on a solid basis.

TABLE 8a

Compositions and Results of the Antimicrobial Activity, Substantivity, Tack, and Incise Drape Adhesion for Examples 54-57P

| Component (Amount in wt-% solids) | Example Number | | | | | |
|---|---|---|---|---|---|---|
|  | 54 | 55 | 55P[1] | 56 | 57 | 57P |
| 75/20/5 of 2-EHA/ DMAEAMC/ AM-90G | 5.00 | 5.00 | 5.00 | 5.00 | 5.00 | 5.00 |
| PVP-I | 7.50 | 7.50 | 0.00 | 7.50 | 7.50 | 0.00 |
| PVP 30K | 0.00 | 0.00 | 0.00 | 0.00 | 0.00 | 7.50 |
| POLYSTEP B22 | 5.00 | 0.00 | 0.00 | 0.00 | 0.00 | 0.00 |
| Ethanol | 3.30 | 5.00 | 5.00 | 5.00 | 5.00 | 5.00 |
| Lactic Acid | 6.00 | 5.00 | 5.00 | 0.00 | 3.00 | 3.00 |
| Citric Acid | 0.00 | 6.00 | 6.00 | 8.00 | 3.00 | 3.00 |
| Malic acid | 0.00 | 0.00 | 0.00 | 5.00 | 5.00 | 5.00 |
| NIKKOL TL10 | 0.00 | 5.00 | 5.00 | 5.00 | 5.00 | 5.00 |
| Water | 73.2 | 66.50 | 74.00 | 64.50 | 66.50 | 66.50 |
| pH | 3.5-4 | 3.5-4 | 3-4 | 3-4 | 3-4 | 3-4 |
| Substantivity (sec) | >60 | >60 | >60 | >60 | >60 | >60 |
| Tack | High | Moderate |  | Low | Moderate |  |
| Microbial kill (log reduction) | 1.9 | 2.35 | 0.6 | 1.9 | 1.8 | 1.4 |
| Incise Drape Adhesion (g/2.54 cm) |  | 36 |  |  |  |  |
| BETADINE kill (log reduction) | 2.5 | 2.3 | 2.3 | 2.3 | 2.3 | 2.3 |

[1]Placebo of Example with same number

TABLE 8b

Compositions and Results of the Antimicrobial Activity, Substantivity and Tack for Examples 58-63.

| Component (Amount in wt-%) | Example Number | | | | | |
|---|---|---|---|---|---|---|
|  | 58 | 59 | 60 | 61 | 62 | 63 |
| 75/20/5 of 2-EHA/ DMAEAMC/ AM-90G | 3.50 | 3.50 | 3.50 | 3.50 | 3.50 | 2.50 |
| PVP-I | 6.50 | 7.50 | 7.50 | 7.50 | 7.50 | 7.50 |
| Ethanol | 5.00 | 3.00 | 3.00 | 0.00 | 0.00 | 0.00 |
| Lactic Acid | 5.00 | 4.00 | 5.00 | 5.00 | 4.00 | 4.50 |
| Citric Acid | 3.00 | 0.00 | 3.00 | 1.00 | 0.00 | 0.00 |
| Malic acid | 0.50 | 4.00 | 3.00 | 3.00 | 3.00 | 2.50 |
| NIKKOL TL10 | 3.50 | 1.25 | 1.25 | 1.25 | 1.25 | 1.25 |
| BRIJ 700 | 0.00 | 1.00 | 0.00 | 1.00 | 1.00 | 1.00 |
| PLURONIC F127 | 0.00 | 0.00 | 1.00 | 0.00 | 0.00 | 0.00 |
| PLURONIC L64 | 0.00 | 0.00 | 0.00 | 0.00 | 0.30 | 0.30 |
| CELVOL 103 | 0.00 | 0.00 | 0.00 | 0.00 | 0.00 | 0.80 |
| SILWET L-7614 | 0.00 | 1.00 | 0.00 | 0.00 | 0.00 | 0.00 |
| Water | 73.00 | 74.75 | 72.75 | 77.75 | 79.45 | 79.65 |
| pH | 3-4 | 3-4 | 3-4 | 3-4 | 3-4 | 3-4 |
| Substantivity (sec) | >60 | >60 | >60 | >60 | >60 |  |
| Tack |  | Low | Moderate | Moderate | Moderate | Low |
| Microbial kill (log reduction) | 2.2 | 2.4 | 2.0 | 2.4 | 1.3 | 1.1 |
| BETADINE kill (log reduction) | 1.9 | 1.9 | 1.9 | 1.9 | 1.7 | 1.7 |

Results: Example 54 illustrates a composition with a quaternary ammonium side-chain polyacrylate film-forming polymer in combination with an anionic surfactant and relatively high level of lactic acid. The composition was found to be stable to prolonged storage (greater than 30 days) at 4° C., 45° C., 50° C., and 60° C. The composition was checked for antimicrobial activity twice. While the average log reduction appears less than BETADINE scrub and paint solutions, the composition had biocidal activity statistically equivalent to BETADINE due to variability in the test method. This is surprising since the compositions of the present invention had a much abbreviated application time (2.5 min total contact time for Example 54 vs. a 5-min scrub with BETADINE Surgical Scrub followed by blotting, painting with BETADINE Solution, and allowing this to dry for a total time of greater than 7 min) Examples 55, 55P (placebo), 56, 57, 57P (placebo) and 58 illustrate the use of a highly concentrated buffer systems based on lactic acid, malic acid, and citric acid in combination with the quaternary ammonium side-chain functional polymer in the presence of a nonionic surfactant. The compositions were found to be stable after 1 week of storage at 60° C. As expected, the active compositions, Examples 55 and 57, had better microbial kill than did the placebos, Example 55P and 57P. The "kill" of the placebo samples may be due to simply removing bacteria due to the application of the composition and subsequent sampling of the site. Examples 62 and 63 appeared to have relatively low antimicrobial activity apparently due to the presence of the PLURONIC L64. This surfactant has a relatively low HLB (15 reported by BASF, 8 by the standard calculation of % EO/5), which may account for this effect.

Example 54 had relatively high tack. Examples 55, 57, 60, 61, and 62 all had moderate tack. The presence of the citric acid appears to help reduce the tack as seen in Example 56. The use of silicone copolyol surfactants also appears to reduce tack, however, Example 59 had low qualitative incise drape adhesion whereas Examples 60 and 61 had good qualitative incise drape adhesion. Example 63 also had lower tack due to the lower level of polyacrylate film-forming polymer and the presence of the PVA.

Example 55 was also evaluated in the quantitative adhesion test and found to remove easier than an incise drape applied over BETADINE scrub and paint solutions (36 vs. 55 g/2.54 cm).

All active containing formulations were applied to human skin and found to wet well and coat uniformly. The compositions could be easily painted uniformly on human skin due to the low viscosity. The dried films formed on skin were flexible, durable, and did not crack. The substantivity of all formulations was excellent with substantivity values greater than 60 seconds. Despite the good substantivity the samples could be easily removed by wiping with a wet paper towel. Furthermore, despite the lower polymer level (polymer/active ratio of 0.47 vs. a polymer/active ratio of 0.67 in Examples 54-57) in Examples 58-62, the compositions still had very good substantivity.

Examples 64-66

Examples 64-66 illustrate the use of a quaternary ammonium side-chain functional polymer, which is not a PSA at room temperature due to the high level of higher glass transition monomers (addition of MMA). These compositions were prepared as outlined above for Preparation Polymer A and the General Composition Preparation using the components listed in Table 9. Compositions were evaluated for human skin antimicrobial activity on human volunteers as described in the test protocol using the 3-wipe paint application technique. Compositions were also evaluated for substantivity and tack as outlined in the test protocols. The results are shown in Table 9. All component quantities are shown on a solids basis.

TABLE 9

Compositions and Results of the Antimicrobial Activity, Substantivity, and Tack for Examples 64-66

| Component | Example Number | | | | |
|---|---|---|---|---|---|
| (Amount in wt-%) | 64 | 64P | 65 | 65P | 66 |
| 65/20/5/10 of 2-EHA/ DMAEAMC/ AM-90G/MMA | 3.50 | 3.50 | 3.50 | 3.50 | 3.50 |
| PVP-I | 7.50 | 0.00 | 7.50 | 0.00 | 7.50 |
| PVP 30K | 0.00 | 7.50 | 0.00 | 7.50 | 0.00 |
| Lactic Acid | 4.50 | 4.50 | 4.50 | 4.50 | 5.00 |
| Malic acid | 2.50 | 2.50 | 2.50 | 2.50 | 2.00 |
| NIKKOL TL10 | 2.50 | 2.50 | 1.50 | 1.50 | 1.50 |
| BRIJ 700 | 2.00 | 2.00 | 1.00 | 1.00 | 1.00 |
| CELVOL 103 | 0.50 | 0.50 | 0.50 | 0.50 | 0.00 |
| MACKAM CB-35 | 0.00 | 0.00 | 0.00 | 0.00 | 1.00 |
| Water | 77.00 | 77.00 | 79.00 | 79.00 | 78.50 |
| pH | 3-4 | 3-4 | 3-4 | 3-4 | 3-4 |
| Substantivity (sec) | >60 | | >60 | | >60 |
| Tack | Low | | Low | | Low |
| Microbial kill (log reduction) | 1.70 | 0.80 | 2.60 | 1.10 | 1.70 |
| BETADINE kill (log reduction) | 2.4 | 2.4 | 2.4 | 2.4 | 2.4 |

In general, the tack of these formulations was less than that of Examples 54-63 due to the higher glass transition polymer added (PVA). The microbial kill of Examples 64 and 65 were good and significantly higher than the placebo formulations. Example 65 killed as well as a BETADINE Scrub and paint despite the very short exposure time. This is assisted by the high buffer level present in the samples. All samples had very good substantivity. Despite the good substantivity the samples could be easily removed by wiping with a wet paper towel. The compositions of Examples 64-66 could be easily painted uniformly on human skin due to the low viscosity. The dried films formed on skin were flexible, durable, and did not crack.

Examples 67-74

Examples 67-74 illustrate the use of high levels of organic acid buffer in combination with preferred quaternary amine and amine oxide side-chain functional substantive film-forming polymers. These compositions were prepared as outlined above for Preparation Polymer A (2-EHA) and Preparation Polymer C (LMA) and the General Composition Preparation using the components listed in Table 10a and 10b. The composition of DIAFORMER Z731 was analyzed by carbon NMR (determined by dissolving 100 milligrams (mg) dry polymer in 3 milliters (mL) of a 50 micromolar (µM) $Cr(OOCCH_3)_3$ solution in $CDCl_3$) and found to be: 48.7% amine oxide of dimethylaminoethylmethacrylate, 18.8% IBMA, 20.8% MMA, 6.8% longer chain methacrylate (mixture of lauryl and stearyl), 0.9% dimethylaminoethanol, and 4.0% dimethylaminoethylmethacrylate. At a pH of 4 approximately 100% of the amine oxide groups are protonated as determined by titration.

Compositions were evaluated for human skin antimicrobial activity on human volunteers as described in the test protocol using the 3 wipe paint application technique. Compositions were also evaluated for substantivity and tack as outlined in the test protocols. The results are shown in Table 10a and 10b.

TABLE 10a

Compositions and Results of the Antimicrobial Activity, Substantivity, and Tack for Examples 67-69

| Component | Example Number | | | | | |
|---|---|---|---|---|---|---|
| (Amount in wt-%) | 67 | 67P | 68 | 68P | 69 | 69P |
| 15/35/50 2-EHA/DMAEAMC/MMA | 0.00 | 0.00 | 3.50 | 3.50 | 2.00 | 2.00 |
| 5/10/40/45 LMA/BA/DMAEAMC/MMA | 3.50 | 3.50 | 0.00 | 0.00 | 0.00 | 0.00 |
| DIAFORMER Z-731 | 0.00 | 0.00 | 2.50 | 2.50 | 2.00 | 2.00 |
| PVP-I | 7.50 | 0.00 | 7.50 | 0.00 | 7.50 | 0.00 |
| PVP 30K | 0.00 | 7.50 | 0.00 | 7.50 | 0.00 | 7.5 |
| Lactic Acid | 5.00 | 5.00 | 5.00 | 5.00 | 5.00 | 5.00 |
| Malic Acid | 2.00 | 2.00 | 2.00 | 2.00 | 2.00 | 2.00 |
| NIKKOL TL10 | 1.50 | 1.50 | 1.50 | 1.50 | 1.25 | 1.25 |
| BRIJ 700 | 1.50 | 1.50 | 1.50 | 1.50 | 1.00 | 1.00 |
| Water | 79.00 | 79.00 | 76.50 | 76.50 | 79.25 | 79.25 |
| pH | 3-4 | 3-4 | 3-4 | 3-4 | 3-4 | 3-4 |
| Microbial kill (log reduction) | 2.0 | 0.9 | 1.6 | 0.9 | 1.3 | 1.1 |
| BETADINE kill (log reduction) | 2.3 | 2.3 | 1.8 | 1.8 | 1.8 | 1.8 |
| Substantivity | >60 | | >60 | | >60 | |
| Tack | Very low | | Very low | | Very low | |

TABLE 10b

Compositions and Results of the Antimicrobial Activity, Substantivity, and Tack for Examples 70-74

| Component (Amount in wt-%) | Example Number | | | | | | |
|---|---|---|---|---|---|---|---|
| | 70 | 70P | 71 | 71P | 72 | 73 | 74 |
| 15/35/50 2-EHA/DMAEAMC/MMA | 0.00 | 0.00 | 3.50 | 3.50 | 3.50 | 0.00 | 3.50 |
| 5/10/40/45 LMA/BA/DMAEAMC/MMA | 2.00 | 2.00 | 0.00 | 0.00 | 2.50 | 0.00 | 0.00 |
| DIAFORMER Z-731 | 1.50 | 1.50 | 0.00 | 0.00 | 0.00 | 5.00 | 0.00 |
| PVP-I | 7.50 | 0.00 | 7.50 | 0.00 | 7.50 | 7.50 | 7.50 |
| PVP 30K | 0.00 | 7.50 | 0.00 | 7.50 | 0.00 | 0.00 | 0.00 |
| Lactic Acid | 5.00 | 5.00 | 5.00 | 5.00 | 5.00 | 5.00 | 5.00 |
| Malic Acid | 2.00 | 2.00 | 2.00 | 2.00 | 2.00 | 2.00 | 2.00 |
| NIKKOL TL10 | 1.50 | 1.50 | 1.50 | 1.50 | 1.50 | 1.50 | 1.50 |
| BRIJ 700 | 1.00 | 1.00 | 1.00 | 1.00 | 1.00 | 0.85 | 1.50 |
| Water | 79.5 | 79.5 | 79.50 | 79.50 | 77.00 | 78.15 | 79.50 |
| pH | 3-4 | 3-4 | 3-4 | 3-4 | 3-4 | 3-4 | 3-5 |
| Microbial kill (log reduction) | 1.7 | 0.6 | | | | | |
| BETADINE kill (log reduction) | 2.3 | 2.3 | | | | | |
| Substantivity | >60 | | >60 | | >60 | >60 | >60 |
| Tack | Very low | | Very low | | Very low | Very low | Very low |

The substantivity and tack results of all compositions were excellent. Despite the good substantivity the samples could be easily removed by wiping with a wet paper towel. The microbial kill of Examples 67-70 shows that the iodine containing formulations have good kill (log reduction greater than >1.5) in a panel of 8 participants where the average baseline was only 2.5-3.5) indicating that the high buffer level is promoting rapid antimicrobial activity. Furthermore, the high antimicrobial activity of these examples also demonstrates that the nonionic polyethoxylated alcohol and polyethoxylate sorbitan ester surfactants are compatible with the active ingredient povidone iodine. The placebo formulations (67P-70P) had relatively low microbial kill indicating that the iodine is the primary active ingredient. The viscosity of all of these examples were very low. The viscosity of formulations in Examples 67 and 73 were measured in accordance with the viscosity test and found to be 7.4 and 10 cps, respectively. Visually the viscosity values of the other examples were comparable. The low viscosity dramatically simplifies easy delivery of the prep over skin using a typical sponge type applicator. The compositions of Examples 67-74 could be painted easily and uniformly on human skin due to the low viscosity. The dried films formed on skin were flexible, durable, and did not crack.

Examples 75-77

Examples 75-77 illustrate the effect of the surfactant system on the stability of compositions comprising high levels of organic acid buffer. The quaternary ammonium side-chain functional polymer used in these examples was made according to the procedure of Preparation Polymer A and the General Composition Preparation using the components listed in Table 11. All component quantities are shown on a solids basis.

TABLE 11

Compositions and Stability of Examples 75-77

| Component | Example Number | | |
|---|---|---|---|
| (Amount in wt-%) | 75 | 76 | 77 |
| Citric acid | 5.0 | 5.0 | 5.0 |
| Water | 66.9 | 71.9 | 71.9 |
| Lactic Acid | 5.0 | 5.0 | 5.0 |
| Ethanol | 5.0 | 5.0 | 5.0 |
| NIKKOL TL10 (HLB = 16.7) | 5.0 | 0.0 | 0.0 |
| BRIJ 58 (HLB = 15.7) | 0.6 | 0.0 | 0.0 |
| BRIJ 76 (HLB = 12.4) | 0.0 | 0.6 | 0.0 |
| BRIJ 700 (HLB = 18.8) | 0.0 | 0.0 | 0.6 |
| 75/20/5 2-EHA/DMAEMA.Cl/AM90G | 5.0 | 5.0 | 5.0 |
| Povidone-Iodine USP | 7.5 | 7.5 | 7.5 |
| Surfactant system HLB | 16.6 | 12.4 | 18.8 |
| Stability | stable | unstable | unstable/floating precipitate |

The composition of Example 75 was only stable in the presence of the polysorbate 20 (NIKKOL TL10) at an intermediate HLB value. The high HLB single surfactant system of Example 77 and the low HLB single surfactant system of Example 76 both resulted in unstable compositions.

Examples 78-86

Examples 78-86 further illustrate the importance of HLB to ensure stability of the compositions comprising high organic acid buffer level and a substantive polymer. The polymer was an amine group functional side-chain polymer. The polymer used in these examples was made according to the procedure of Preparation Polymer A and the General Composition Preparation using the components listed in Table 12a and 12b. Compositions were evaluated for stability as described for Examples 22-43, as well as tack and incise drape adhesion as outlined in the test protocols. The results are shown in Table 12a and 12b. All component quantities are shown on a solids basis. The HLB refers to that of the surfactant system.

TABLE 12a

Compositions and Results of the Stability, Tack, and Incise Drape Adhesion for Examples 78-82

| Component (Amount in weight percent) | 78 | 79 | 80 | 81 | 82 |
|---|---|---|---|---|---|
| Citric acid | 3.0 | 0.0 | 3.0 | 0.0 | 2.0 |
| Lactic Acid | 5.0 | 4.0 | 5.0 | 4.0 | 4.0 |
| Malic Acid | 1.0 | 4.0 | 1.0 | 4.0 | 4.0 |
| NIKKOL TL10 | 2.0 | 2.2 | 2.0 | 1.0 | 1.0 |
| BRIJ 700 | 1.0 | 0.0 | 2.0 | 2.0 | 1.0 |
| PLURONIC F68 | 0.0 | 1.0 | 0.0 | 0.0 | 0.0 |
| POLYSTEP B22 | 0.0 | 0.0 | 0.0 | 0.0 | 3.0 |
| 75/20/5 of 2-EHA/DMAEAMC/AM-90G | 3.5 | 3.4 | 3.5 | 3.5 | 3.5 |
| Povidone-Iodine USP | 7.5 | 7.5 | 7.5 | 7.5 | 7.5 |
| Ethanol | 3.0 | 3.0 | 3.0 | 3.0 | 0.0 |
| Water | 74.0 | 74.9 | 73.0 | 75.0 | 74.0 |
| Stability | transparent/stable; color turned a little brown in 1 week | cloudy/mocha color; precipitate after a few days | little precipitation over night at room temp/ stable at 60° C. | | cloudy at room temp/ stable at 60° C. with a muddy color |
| Tack | no tack | | | | |
| Incise Drape Adhesion Test | good adhesion | adhesion better than Example 78 | | | |
| Surfactant System HLB | 17.27 | 20.41 | 17.65 | 18.03 | NA |

TABLE 12b

Compositions and Results of the Stability Test for Examples 83-86

| Component (Amount in weight percent) | 83 | 84 | 85 | 86 |
|---|---|---|---|---|
| Lactic Acid | 4.0 | 4.0 | 4.0 | 4.0 |
| Malic Acid | 4.0 | 4.0 | 4.0 | 4.0 |
| NIKKOL TL10 | 1.0 | 1.0 | 1.0 | 1.0 |
| PLURONIC F127 | 1.0 | 1.0 | 1.0 | 1.0 |
| PLURAFAC A-39 PRILL | 0.0 | 1.0 | 0.0 | 0.0 |
| SURFONIC N-150 | 0.0 | 0.0 | 1.0 | 0.0 |
| PLURONIC P 65 | 0.0 | 0.0 | 0.0 | 1.0 |
| 75/20/5 of 2-EHA/DMAEAMC/AM-90G | 3.5 | 3.5 | 3.5 | 0.0 |
| Povidone-Iodine USP | 7.5 | 7.5 | 7.5 | 7.5 |
| Ethanol | 3.0 | 3.0 | 3.0 | 3.0 |
| Water | 76.0 | 75.0 | 75.0 | 78.5 |
| Stability | dark and transparent/ stable | dark and transparent/ stable | cloudy but stable solution | cloudy but stable solution |
| Surfactant System HLB | 15.75 | 16.75 | 12.25 | 13.25 |

The examples show that compositions with a surfactant system HLB of 12.25-18 were stable. However, it is believed that the most stable compositions are those that result in transparent solutions such as those of examples 78, 83, and 84 which have a surfactant system HLB of 15.75-17.27.

Examples 87-91

Examples 87-91 illustrate the use of a high Tg polymer dissolved in the composition to reduce the tack. The high Tg polyvinyl alcohols (PVAs) added to the compositions were first dissolved as a concentrate in water at 10% by weight by adding the PVA to water and heating in a sealed vessel to 90° C. with occasional agitation until dissolved. The percent hydrolysis and viscosity as reported by Air Products Bulletin for a 4% aqueous solution at 20° C. are shown in Table 13a for the CELVOL polyvinyl alcohols from Celanese Ltd., Dallas, Tex.

TABLE 13a

Percent Hydrolysis and Viscosity for CELVOL Polyvinyl Alcohols

| Polyvinyl Alcohol | Percent Hydrolysis | Viscosity[1] (cps) |
|---|---|---|
| CELVOL 321 | 98-98.8 | 16.5-20.5 |
| CELVOL 103 | 98-98.8 | 3.5-4.5 |
| CELVOL 305 | 98-98.8 | 4.5-5.5 |
| CELVOL 502 | 88 | 3-3.7 |
| CELVOL 523 | 88 | 23-27 |

[1]As reported by Air Products Bulletin for a 4% aqueous solution at 20° C.

The examples were made according to the General Composition Preparation using the components listed in Table 13b. Compositions were evaluated for stability as described for Examples 22-43, as well as, substantivity, tack and incise drape adhesion as outlined in the test protocols. The results are shown in Table 13b. All component quantities are shown on a solids basis.

TABLE 13b

Compositions and Results of Stability, Substantivity, Tack, and Incise Drape Adhesion for Examples 87-91

| Component (Amount in weight percent) | 87 | 88 | 89 | 90 | 91 |
|---|---|---|---|---|---|
| CELVOL 321 (PVA) | 1.00 | 0.00 | 0.00 | 0.00 | 0.00 |
| CELVOL 103 (PVA) | 0.00 | 1.00 | 0.00 | 0.00 | 0.00 |
| CELVOL 305 (PVA) | 0.00 | 0.00 | 1.00 | 0.00 | 0.00 |
| CELVOL 502 (PVA) | 0.00 | 0.00 | 0.00 | 1.00 | 0.00 |
| CELVOL 523 (PVA) | 0.00 | 0.00 | 0.00 | 0.00 | 1.00 |
| Water | 79.50 | 79.50 | 79.50 | 79.50 | 79.64 |
| Lactic Acid | 4.48 | 4.48 | 4.48 | 4.48 | 4.49 |
| Malic Acid | 2.50 | 2.50 | 2.50 | 2.50 | 2.50 |

TABLE 13b-continued

Compositions and Results of Stability, Substantivity, Tack, and Incise Drape Adhesion for Examples 87-91

| Component (Amount in weight percent) | Example Number | | | | |
|---|---|---|---|---|---|
| | 87 | 88 | 89 | 90 | 91 |
| NIKKOL TL10 | 1.50 | 1.50 | 1.50 | 1.50 | 1.50 |
| BRIJ 700 | 1.02 | 1.02 | 1.02 | 1.02 | 0.87 |
| 75/20/5 of 2-EHA/ DMAEAMC/ AM-90G | 2.50 | 2.50 | 2.50 | 2.50 | 2.50 |
| Povidone-Iodine USP | 7.50 | 7.50 | 7.50 | 7.50 | 7.50 |
| Stability at 23° C. | Good | Very good | Poor | Very good | Poor |
| Substantivity | Very good | Very good | | Good | |
| Tack | Low | Very low | Low | Very low | Low |
| Incise Drape Adhesion | | Good | | Good | |
| Surfactant System HLB | 17.6 | 17.6 | 17.6 | 17.6 | 17.6 |

The substantivity of Examples 87 and 88 containing PVA with a very high degree of hydrolysis was very good. Note that the PVA components of these formulations are not cold water soluble due to the high degree of hydrolysis. Despite the good substantivity the samples could be easily removed by wiping with a wet paper towel.

Example 88 appeared to have the best adhesion of a PSA-coated product (incise drape) as tested by the qualitative test described above. It is not clear why the CELVOL 305 and 523 compositions were not stable in Examples 89 and 91.

Examples 92-97

Examples 92-97 illustrate the use of high levels of an organic acid buffer in combination with an amine oxide side-chain functional substantive film-forming polymer. The polymer used in Examples 92-94 was a commercially available poly(amine oxide acrylate) available as DIAFORMER Z-731 (Clariant Corp.). The polymer used in Examples 95-97 was prepared as outlined above for Preparation of Polymer C (LMA). The polymer included SMA (10%)/iBMA (25%)/ DMAEMA (55%)/MMA(10%). The monomers were polymerized at a temperature of 65° C. using 0.3% by weight VAZO 67. The DMAEMA was oxidized to the amine oxide using a molar ratio of DMAEMA to hydrogen peroxide used was 0.9. Residual monomer was scavenged with vitamin C in place of SFS. After distillation the residual level of hydrogen peroxide was measured and found to be less than 100 ppm. The polymer had an inherent viscosity of 0.7. The compositions were prepared according to the General Composition Preparation using the components listed in Table 14.

Compositions were evaluated for human skin antimicrobial activity on human volunteers as described in the test protocol using the 30 second scrub application technique. Compositions were also evaluated for substantivity, drape adhesion, and tack as outlined in the test protocols. The results are shown in Table 14.

TABLE 14

Compositions and Results of the Antimicrobial Activity, Substantivity, and Tack for Examples 92-97

| Component (Amount in wt-% solids) | Example Number | | | | | |
|---|---|---|---|---|---|---|
| | 92 | 93 | 94 | 95 | 96 | 97 |
| 5/10/40/45 SMA/iBMA/ DMAEMA oxide/MMA | 0.00 | 0.00 | 0.00 | 5.00 | 5.00 | 5.00 |
| DIAFORMER Z-731 | 5.00 | 5.00 | 5.00 | 0.00 | 0.00 | 0.00 |
| PVP-I | 7.50 | 7.50 | 7.50 | 0.00 | 7.50 | 0.00 |
| Lactic Acid | 5.00 | 5.00 | 5.00 | 5.00 | 5.00 | 5.00 |
| Malic Acid | 2.00 | 2.00 | 2.00 | 2.00 | 2.00 | 2.00 |
| BRIJ 700 | 1.00 | 1.00 | 1.00 | 1.00 | 1.00 | 1.00 |
| Mackam 50-SB | 1.00 | 0.00 | 0.00 | 1.00 | 0.00 | 0.00 |
| CRODAPHOS SG | 0.00 | 0.00 | 1.00 | 0.00 | 0.00 | 1.00 |
| STEPANMILD SL3 | 0.00 | 0.67 | 0.00 | 0.00 | 0.67 | 0.00 |
| AMMONYX LMDO | 0.00 | 0.00 | 1.00 | 0.00 | 0.00 | 1.00 |
| Water | 78.5 | 78.83 | 77.50 | 78.5 | 78.83 | 77.5 |
| pH | 3.5-4 | 3.5-4 | 3.5-4 | 3.5-4 | 3.5-4 | 3.5-4 |
| Microbial kill (log reduction) | 1.9 | 2.6 | 2.5 | | | |
| BETADINE kill (log reduction) | 1.7 | 1.7 | 1.7 | | | |
| Drape Adhesion | Good | Good | Good | | | |
| Substantivity (sec) | >60 | 50-60 | 50 | >60 | >60 | 30 |
| Tack | Very low | Very low | Very low | Very low | Very low | Very low |

The results indicate that Examples 92-94 had very good antimicrobial activity. Examples 92, 95, and 96 had exceptional substantivity. The substantivity of Examples 93, 94 and 97 was far greater than that of BETADINE SOLUTION which typically lasts less than 10 seconds. The tack of all samples was very low. The adhesion of IOBAN 2 Incise drape (Drape Adhesion) was good for Examples 92-94 and judged to be equivalent to that over dry BETADINE Solution. All samples were transparent and dark (stable) at room temperature.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A skin antisepsis composition comprising:
   a vehicle comprising a (C1-C4)alcohol and water in a ratio of at least 60:40;
   a hydroxycarboxylic acid, wherein the hydroxycarboxylic acid is present in an amount of at least 5 weight percent, based upon the total weight of the composition;
   a surfactant;
   a cationic film-forming polymer having side chain functional amine groups; and
   at least one antimicrobial agent; and
   wherein the cationic film-forming polymer has at least 300 grams and not greater than 3000 grams polymer per equivalent of amine group; and wherein the at least one antimicrobial agent is selected from the group consisting of iodine, triiodide, iodophors, and combinations thereof.

2. The composition of claim 1, wherein the (C1-C4)alcohol is selected from the group consisting of ethanol, isopropanol, n-propanol, and mixtures thereof.

3. The composition of claim 1, wherein the hydroxycarboxylic acid includes one or more compounds represented by the formula:

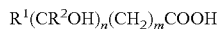
$$R^1(CR^2OH)_n(CH_2)_mCOOH$$

wherein: $R^1$ and $R^2$ are each independently H or a (C1-C8) alkyl group (saturated straight, branched, or cyclic group), a (C6-C12)aryl, or a (C6-C12)aralkyl or alkaryl group (saturated straight, branched, or cyclic alkyl group), wherein $R^1$ and $R^2$ may be optionally substituted with one or more carboxylic acid groups; m=0 or 1; and n=1-3, preferably, n=1-2.

4. The composition of claim 1 having a pH of 3 to about 4.5.

5. The composition of claim 1, wherein the hydroxycarboxylic acid is selected from the group consisting of lactic acid, malic acid, citric acid, 2-hydroxybutanoic acid, 3-hydroxybutanoic acid, mandelic acid, gluconic acid, tartaric acid, salicylic acid, each of which is unsubstituted or substituted with at least one hydroxyl, phenyl, hydroxyphenyl, alkyl, or halogen group, and combinations thereof.

6. The composition of claim 1, wherein the cationic polymer includes side-chain functional amine groups selected from the group consisting of protonated tertiary amines, quaternary amines, amine oxides, and combinations thereof.

7. The composition of claim 1, wherein the surfactant is selected from the group nonionic, anionic, or amphoteric surfactants.

8. The composition of claim 7, wherein the surfactant is a nonionic surfactant with an HLB value of at least 14.

9. The composition of claim 8, wherein the surfactant is a nonionic surfactant with an HLB value of no greater than 19.

10. The composition of claim 7 wherein the surfactant is an anionic or amphoteric surfactant.

11. The composition of claim 10 wherein the anionic or amphoteric surfactant is selected from the group consisting of sulfonates, sulfates, phosphates, phosphonates, and ammonium sulfonate amphoterics, and mixtures thereof.

12. The composition of claim 11 wherein the anionic surfactant comprises a polyalkoxylate group.

13. The antiseptic composition of claim 7 wherein the surfactant is an amine oxide.

14. The composition of claim 1 further comprising a skin emollient and/or humectant.

15. A method of disinfecting tissue comprising:
 applying the composition of claim 1 to tissue, wherein the composition is not diluted; and
 allowing the composition to remain on the tissue for a time sufficient to reduce bacterial load on the tissue.

16. The method of claim 15, further comprising:
 drying the applied composition to form a film of the dried composition; and
 placing a PSA-coated article over the film of the dried composition.

* * * * *